United States Patent
Vakkalanka et al.

(10) Patent No.: US 10,981,919 B2
(45) Date of Patent: *Apr. 20, 2021

(54) SELECTIVE PI3K DELTA INHIBITORS

(71) Applicant: Rhizen Pharmaceuticals SA, Basel (CH)

(72) Inventors: Swaroop K. Vakkalanka, La Chaux-de-Fonds (CH); Meyyappan Muthuppalaniappan, Hyderabad (IN); Dhanapalan Nagarathnam, Bethany, CT (US)

(73) Assignee: Rhizen Pharmaceuticals SA, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/776,327

(22) Filed: Jan. 29, 2020

(65) Prior Publication Data

US 2020/0270258 A1 Aug. 27, 2020

Related U.S. Application Data

(63) Continuation of application No. 16/109,337, filed on Aug. 22, 2018, now Pat. No. 10,570,142, which is a continuation of application No. 15/480,128, filed on Apr. 5, 2017, now Pat. No. 10,072,013, which is a continuation of application No. 15/283,515, filed on Oct. 3, 2016, now Pat. No. 9,669,033, which is a continuation of application No. 14/832,962, filed on Aug. 21, 2015, now Pat. No. 9,475,818, which is a continuation of application No. 13/933,856, filed on Jul. 2, 2013, now Pat. No. 9,150,579.

(60) Provisional application No. 61/691,561, filed on Aug. 21, 2012, provisional application No. 61/691,586, filed on Aug. 21, 2012.

(30) Foreign Application Priority Data

Jul. 4, 2012 (IN) ............................ 2692/CHE/2012
Jul. 4, 2012 (IN) ............................ 2693/CHE/2012

(51) Int. Cl.
| | | |
|---|---|---|
| C07D 487/04 | (2006.01) | |
| A61K 31/519 | (2006.01) | |
| A61P 35/00 | (2006.01) | |
| A61K 45/06 | (2006.01) | |
| C12N 9/12 | (2006.01) | |

(52) U.S. Cl.
CPC .......... *C07D 487/04* (2013.01); *A61K 31/519* (2013.01); *A61K 45/06* (2013.01); *A61P 35/00* (2018.01); *C12N 9/1205* (2013.01); *C12Y 207/01137* (2013.01); *Y02A 50/30* (2018.01)

(58) Field of Classification Search
CPC ...... C07D 487/04; A61K 31/519; A61P 35/00
USPC ........................................ 544/262; 514/262.1
See application file for complete search history.

(56) References Cited

U.S. PATENT DOCUMENTS

| | | | |
|---|---|---|---|
| 4,841,077 A | 6/1989 | Ito et al. | |
| 6,403,588 B1 | 6/2002 | Hayakawa et al. | |
| 6,608,053 B2 | 8/2003 | Hayakawa et al. | |
| 6,608,056 B1 | 8/2003 | Hayakawa et al. | |
| 6,653,320 B2 | 11/2003 | Hayakawa et al. | |
| 6,703,414 B2 | 3/2004 | Powis et al. | |
| 6,770,641 B2 | 8/2004 | Hayakawa et al. | |
| 6,838,457 B2 | 1/2005 | Hayakawa et al. | |
| 7,037,915 B2 | 5/2006 | Hayakawa et al. | |
| 7,173,029 B2 | 2/2007 | Hayakawa et al. | |
| 7,589,101 B2 | 9/2009 | Okram et al. | |
| 7,592,342 B2 | 9/2009 | Feng et al. | |
| 7,595,320 B2 | 9/2009 | Barberis et al. | |
| 7,595,330 B2 | 9/2009 | Cheung et al. | |
| 7,598,245 B2 | 10/2009 | Arnost et al. | |
| 7,601,718 B2 | 10/2009 | Green et al. | |
| 7,601,724 B2 | 10/2009 | Guzi et al. | |
| 7,605,155 B2 | 10/2009 | Guzi et al. | |
| 7,605,160 B2 | 10/2009 | Fink et al. | |
| 7,608,622 B2 | 10/2009 | Liu et al. | |
| 9,150,579 B2 | 10/2015 | Vakkalanka et al. | |
| 9,475,818 B2 | 10/2016 | Vakkalanka et al. | |
| 9,669,033 B2 | 6/2017 | Vakkalanka et al. | |
| 10,072,013 B2 | 9/2018 | Vakkalanka et al. | |
| 10,570,142 B2 * | 2/2020 | Vakkalanka | A61P 9/12 |
| 2003/0149074 A1 | 8/2003 | Melese et al. | |
| 2003/0158212 A1 | 8/2003 | Melese et al. | |
| 2004/0053946 A1 | 3/2004 | Lackey et al. | |
| 2004/0082638 A1 | 4/2004 | McDonald et al. | |
| 2004/0092561 A1 | 5/2004 | Ruckle et al. | |
| 2006/0270673 A1 | 11/2006 | Duggan et al. | |
| 2008/0039459 A1 | 2/2008 | Folkes et al. | |

(Continued)

FOREIGN PATENT DOCUMENTS

| | | |
|---|---|---|
| EP | 0245518 A1 | 11/1987 |
| EP | 1417976 A1 | 5/2004 |

(Continued)

OTHER PUBLICATIONS

International Search Report issued in PCT/IB2013/055434 dated Sep. 30, 2013.
Banker, G.S., et al., Modern Pharmaceuticas, 3ED, Marcel Dekker, New York, 1996, p. 596.
Daia g e et al., The Directed Lithiation of Some 3-Acylchromone Acetals, Tetrahedron Letters, Elsevier, Amsterdam, NL, vol. 39, No. 10, Mar. 5, 1998, pp. 1215-1218.

(Continued)

*Primary Examiner* — Venkataraman Balasubramanian
(74) *Attorney, Agent, or Firm* — Blank Rome LLP

(57) ABSTRACT

The present invention relates to selective inhibitors of PI3K delta protein kinases, methods of preparing them, pharmaceutical compositions containing them and methods of treatment and/or prevention of kinase mediated diseases or disorders with them.

13 Claims, 2 Drawing Sheets

(56) References Cited

U.S. PATENT DOCUMENTS

| | | |
|---|---|---|
| 2008/0076768 A1 | 3/2008 | Chuckowree et al. |
| 2008/0207611 A1 | 8/2008 | Shuttleworth et al. |
| 2009/0233926 A1 | 9/2009 | Butterworth et al. |
| 2009/0233950 A1 | 9/2009 | Jung et al. |
| 2009/0234132 A1 | 9/2009 | Budd et al. |
| 2009/0238828 A1 | 9/2009 | Munzert et al. |
| 2009/0239847 A1 | 9/2009 | Bruce et al. |
| 2009/0239859 A1 | 9/2009 | Chua et al. |
| 2009/0239936 A1 | 9/2009 | Sugimoto et al. |
| 2009/0247538 A1 | 10/2009 | Berdini et al. |
| 2009/0247554 A1 | 10/2009 | Dong et al. |
| 2009/0247565 A1 | 10/2009 | Lim et al. |
| 2009/0247567 A1 | 10/2009 | Do et al. |
| 2009/0258852 A1 | 10/2009 | Arrington et al. |
| 2009/0263397 A1 | 10/2009 | Buck et al. |
| 2009/0263398 A1 | 10/2009 | Lyons et al. |
| 2009/0270430 A1 | 10/2009 | Baik et al. |
| 2009/0270445 A1 | 10/2009 | Zeng et al. |
| 2009/0270621 A1 | 10/2009 | Wallace et al. |
| 2010/0249155 A1 | 9/2010 | Evarts et al. |
| 2011/0118257 A1 | 5/2011 | Muthuppalaniappan et al. |
| 2012/0059001 A1 | 3/2012 | Muthuppalaniappan et al. |

FOREIGN PATENT DOCUMENTS

| | | |
|---|---|---|
| JP | 08175990 A | 7/1996 |
| JP | 08176070 A | 7/1996 |
| JP | 2001247477 A | 9/2001 |
| WO | WO-2003034997 A2 | 5/2003 |
| WO | WO-2003035618 A2 | 5/2003 |
| WO | WO-2003037886 A2 | 5/2003 |
| WO | WO-2004006916 A1 | 1/2004 |
| WO | WO-2004007491 A1 | 1/2004 |
| WO | WO-2004017950 A2 | 3/2004 |
| WO | WO-2006046031 A1 | 5/2006 |
| WO | WO-2006046035 A1 | 5/2006 |
| WO | WO-2006046040 A1 | 5/2006 |
| WO | WO-2007042806 A1 | 4/2007 |
| WO | WO-2007042810 A1 | 4/2007 |
| WO | WO-2008070740 A1 | 6/2008 |
| WO | WO-2008073785 A2 | 6/2008 |
| WO | WO-2009105712 A1 | 8/2009 |
| WO | WO-2009109867 A2 | 9/2009 |
| WO | WO-2009111531 A1 | 9/2009 |
| WO | WO-2009111547 A1 | 9/2009 |
| WO | WO-2009112565 A1 | 9/2009 |
| WO | WO-2009114870 A2 | 9/2009 |
| WO | WO-2009114874 A2 | 9/2009 |
| WO | WO-2009117097 A1 | 9/2009 |
| WO | WO-2009117482 A1 | 9/2009 |
| WO | WO-2009120094 A2 | 10/2009 |
| WO | WO-2009126635 A1 | 10/2009 |
| WO | WO-2009129211 A1 | 10/2009 |
| WO | WO-2009129259 A2 | 10/2009 |
| WO | WO-2010111432 A1 | 9/2010 |
| WO | WO-2011055215 A2 | 5/2011 |

OTHER PUBLICATIONS

Ellis G P et al: "Benzopyrones. 14. Synthesis and Antialergic Properties of Some N-Tetrazolylcarboxamides and Related Compounds". Journal of Medicinal Chemistry. American Chemical Society. US. vol. 21. No. 11. Jan. 1, 1978 (Jan. 1, 1978). pp. 1120-1126. XPOOI055197. ISSN: 0022-2623. DOI: DOI:I0.I021/JM00209A006 table 1; compounds 27.28.

Iijima I E et al, Synthesis Utilizing the Beta Carbonyl System 5, a Synthesis Directed Toward the Fungal Xanthone Bikaverin, Journal of the Chemical Society, Perkin Transaction 1, Chemical Society, Letchworth, GB, No. 12, Jan. 1, 1979, pp. 3190-3195.

Kawase et al., Bulletin of the Chemical Society of Japan, 1962, 35, pp. 1366-1369.

Ogawara H et al: "Inhibition of Tyrosine Protein Kinase Activity by Synthetic Isoflavones and Flavones", Journal of Antibiotics, Japan Antibiotics Research Association, Tokyo, JP, vol. 1. 42, No. 2, Feb. 1, 1989 (Feb. 1, 1989), pp. 340-343, XP009028517, ISSN: 0021-8820 p. 340; compounds PKI-17, PKI-24 p. 340, left column; p. 341, right column.

Williams A C et al., Product Class 4: Benzopyranones and Benzopyranthiones, Jan. 1, 2003, Science of Synthesis, pp. 347-638.

Wolff, Mandred E., Burger's Medicinal Chemistry, 53D, Part I, John Wiley & Sons, 1995, pp. 975-977.

Cecil Textbook of Medicine, edited by Bennet, J.C., and Plum F., 20th Edition, vol. 1, 1004-101 O, 1996.

Cohen, et al., Current Opinion in Chemical Biology, 3, 59-465, 1999.

Dermer, et al., Bio/Technology, 1994, 12:320.

Fabbro, et al., Pharmacology & Therapeutics 93, 79-98, 2002.

Ferrara, N, Oncology, 69 Suppl. 3, 11-16, 2005.

Freshney, et al., Culture of Animal Cells, A Manual of Basic Technique, Alan R. Liss, Inc., 1983, New York, p. 4.

Gautschi, et al, Clin. Cancer Res., 14(6), 1639-1648, 2008.

Golub, et al., Science, 286, 531-537, 1999.

Jain, et al., Nature Clinical Practice Oncology, 3(1), 24-40, 2006.

Mass, R.D., Int. J. Radiation Oncology Bio. Phys. vol. 58(3): 932-+40, 2004.

Mountzios, et al., Cancer Treatments Reviews, 34, 175-182, 2008.

Porta, et al., Front Oncol. Apr. 14, 2014, 4:64:1-11.

Pyne, et al., Cancer Res 2011, 71:6576-6582.

Qui, Y, Oncogene, 19, 5651-5661, 2000.

\* cited by examiner

SELECTIVE PI3K DELTA INHIBITORS

The present application is a continuation of U.S. patent application Ser. No. 16/109,337, filed Aug. 22, 2018, which is a continuation of U.S. patent application Ser. No. 15/480, 128, filed Apr. 5, 2017, now U.S. Pat. No. 10,072,013, which is a continuation of U.S. patent application Ser. No. 15/283, 515, filed Oct. 3, 2016, now U.S. Pat. No. 9,669,033, which is a continuation of U.S. patent application Ser. No. 14/832, 962, filed Aug. 21, 2015, now U.S. Pat. No. 9,475,818, which is a continuation of U.S. patent application Ser. No. 13/933,856, filed Jul. 2, 2013, now U.S. Pat. No. 9,150,579, which claims the benefit of Indian Patent Application Nos. 2692/CHE/2012, filed Jul. 4, 2012, and 2693/CHE/2012, filed Jul. 4, 2012, and U.S. Provisional Application Nos. 61/691,561, filed Aug. 21, 2012, and 61/691,856, filed Aug. 21, 2012, each of which is hereby incorporated by reference in its entirety.

FIELD OF THE INVENTION

The present invention relates to selective inhibitors of PI3K delta protein kinases, methods of preparing them, pharmaceutical compositions containing them and methods of treatment and/or prevention of kinase mediated diseases or disorders with them.

BACKGROUND OF THE INVENTION

Phosphatidylinositol (hereinafter abbreviated as "PI") is one of a number of phospholipids found in cell membranes. In recent years it has become clear that PI plays an important role in intracellular signal transduction. Cell signaling via 3'-phosphorylated phosphoinositides has been implicated in a variety of cellular processes, e.g., malignant transformation, growth factor signaling, inflammation, and immunity (Rameh et al. (1999) *J. Biol Chem,* 274:8347-8350). The enzyme responsible for generating these phosphorylated signaling products, phosphatidylinositol 3-kinase (also referred to as PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al. (1992) *Trends Cell Biol* 2:358-60).

The phosphoinositide 3-kinases (PI3Ks) are a family of enzymes that regulate diverse biological functions in every cell type by generating phosphoinositide second-messenger molecules. As the activity of these phosphoinositide second messengers is determined by their phosphorylation state, the kinases and phosphatises that act to modify these lipids are central to the correct execution of intracellular signaling events. Phosphoinositide 3-kinases (PI3K) phosphorylate lipids at the 3-hydroxyl residue of an inositol ring (Whitman et al. (1988) *Nature,* 332:664) to generate phosphorylated phospholipids (PIP3s) which act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al. (2002) *Nature Rev. Cancer* 2:489; Phillips et al. (1998) *Cancer* 83:41).

The members of the class I family of PI3Ks are dimers of a regulatory and a catalytic subunit. The class I family consists of four isoforms, determined by the 110 kDa catalytic subunits α, β, γ and δ. Engelman J A, *Nat Rev Genet* 2006; 7:606-19; Carnero A, *Curr Cancer Drug Targets* 2008; 8:187-98; Vanhaesebroeck B, *Trends Biochem Sci* 2005; 30:194-204. Class I can be subdivided into two subclasses: Ia, formed by the combination of p110 α, β, and δ and a regulatory subunit (p85, p55 or p50) and Ib, formed by p110 γ and p101 regulatory subunits.

There is considerable evidence indicating that Class Ia PI3K enzymes contribute to tumourigenesis in a wide variety of human cancers, either directly or indirectly (Vivanco and Sawyers, *Nature Reviews Cancer,* 2002, 2, 489-501; Marone et al., *Biochimica et Biophysica Acta* 1784 (2008) 159-185). In particular, the p110 delta isoform has been implicated in biological functions related to immune-inflammatory diseases, including signaling from the B-cell receptor, T cell receptor, FcR signaling of mast cells and monocyte/macrophage, and osteoclast function/RANKL signaling (Deane J and Fruman D A (2004) *Annu Rev. Immunol.* 2004. 22:563-98; Janas et al., *The Journal of Immunology,* 2008, 180: 739-746; Marone R et al., *Biochim. Biophy. Acta* 2007, 1784:159-185). Deletion of the PI3K delta gene or selective introduction of a catalytically inactive mutant of PI3K delta causes a nearly complete ablation of B cell proliferation and signaling, and impairment of signaling through T cells as well.

There still remains an unmet and dire need for small molecule kinase modulators in order to regulate and/or modulate transduction of kinases, particularly PI3K, for the treatment of diseases and disorders associated with kinase-mediated events.

International Publication No. WO 2011/055215 and U.S. Patent Publication No. 2011/0118257 disclose certain 2,3 disubstituted-4H-chromen-4-one as PI3K kinase modulators and are incorporated herein by reference in their entirety for all purposes.

SUMMARY OF THE INVENTION

The present invention is directed to selective inhibitors of PI3K delta protein kinases. These compounds are suitable for use in a pharmaceutical composition for the treatment of a PI3K associated disease, disorder or condition, e.g., a proliferative disease such as cancer.

In one embodiment, the PI3K delta inhibitor is (S)-2-(1-(4-amino-3-(3-fluoro-4-isopropoxyphenyl) -1H-pyrazolo[3,4-d]pyrimidin-1-yl)ethyl)-3-(3-fluorophenyl)-4H-chromen-4-one (compound-A1) or a pharmaceutically acceptable salt thereof. In another embodiment, the PI3K delta inhibitor is (R)-2-(1-(4-amino-3-(3-fluoro-4-isopropoxyphenyl) -1H-pyrazolo[3,4-d]pyrimidin-1-yl)ethyl)-3-(3-fluorophenyl)-4H-chromen-4-one (compound-A2) or a pharmaceutically acceptable salt thereof.

In yet another embodiment, the PI3K delta inhibitor is 2-(1-(4-amino-3-(3-fluoro-4-isopropoxyphenyl) -1H-pyrazolo[3,4-d]pyrimidin-1-yl)ethyl)-6-fluoro-3-(3-fluorophenyl)-4H-chromen-4-one (compound-B) or a pharmaceutically acceptable salt thereof. The present invention also includes compound-B, and its pharmaceutically acceptable salts, in racemic form as well as their stereoisomers, (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one (compound-B1), (R)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one (compound-B2), and pharmaceutically acceptable salts thereof.

In one embodiment, the PI3K delta inhibitor is (S)-2-(1-(4-amino-3-(3-fluoro-4-isopropoxyphenyl) -1H-pyrazolo[3,4-d]pyrimidin-1-yl)ethyl)-6-fluoro-3-(3-fluorophenyl)-4H-chromen -4-one 4-methylbenzenesulfonate. In another embodiment, the PI3K delta inhibitor is (S)-2-(1-(4-amino-3-(3-fluoro-4-isopropoxyphenyl)-1H-pyrazolo[3,4-d]pyrimidin-1-yl)ethyl) -6-fluoro-3-(3-fluorophenyl)-4H-chromen-4-one sulphate. In another embodiment, the PI3K delta inhibitor is (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one hydrochloride. In another embodiment, the PI3K delta inhibitor is (S)-2-(1-(4-amino-3-(3-fluoro -4-isopropoxyphenyl)-1H-pyrazolo[3,4-d]pyrimidin-1-yl)ethyl)-6-fluoro-3-(3-fluorophenyl) -4H-chromen-4-one benzenesulfonate. In another embodiment, the PI3K delta inhibitor is (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one maleate. In another embodiment, the PI3K delta inhibitor is (S)-2-(1-(4-amino-3-(3-fluoro-4-isopropoxyphenyl) -1H-pyrazolo[3,4-d]pyrimidin-1-yl)ethyl)-6-fluoro-3-(3-fluorophenyl)-4H-chromen-4-one camphor sulphonate.

The chemical structures of compounds A1, A2, B, B1, and B2 are shown below.

(A1)

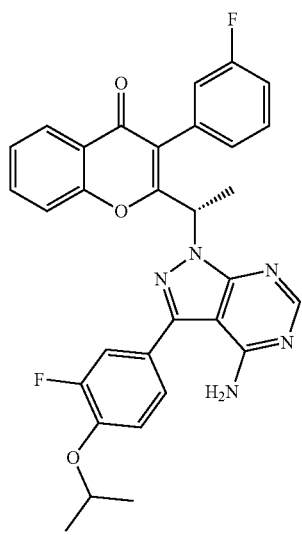

(A2)

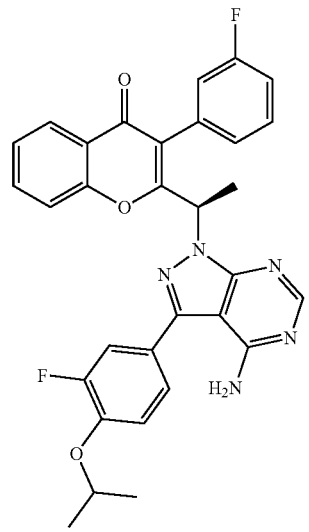

(B)

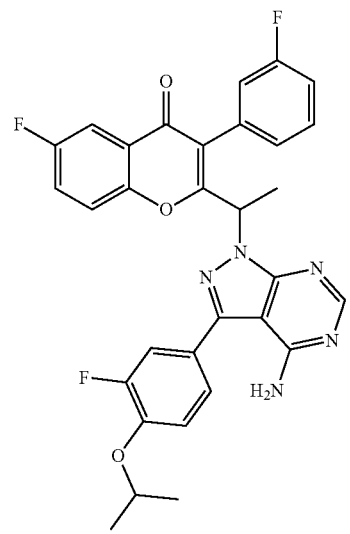

(B1)

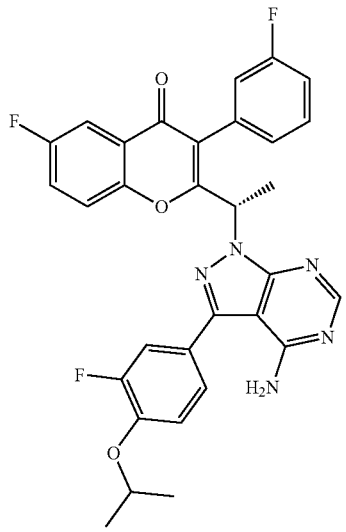

-continued

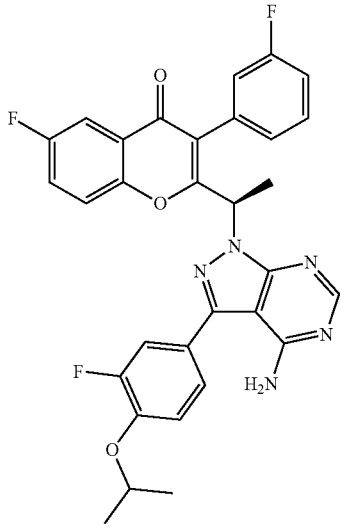

(B2)

In one preferred embodiment, the present invention relates to the compound (S)-2-(1-(4-amino-3-(3-fluoro-4-isopropoxyphenyl)-1H-pyrazolo[3,4-d]pyrimidin-1-yl)ethyl)-3-(3-fluorophenyl)-4H-chromen-4-one (compound-A1) or a pharmaceutically acceptable salt thereof.

In another preferred embodiment, the present invention relates to the compound (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one (compound-B1) or a pharmaceutically acceptable salt thereof.

The present invention also encompasses prodrugs of these compounds.

The invention further provides a pharmaceutical composition comprising one or more compounds of the present invention (such as compound A1, A2, B, B1, B2, pharmaceutically acceptable salts thereof, or mixtures thereof) together with a pharmaceutically acceptable carrier. The pharmaceutical composition may further comprise one or more of additional active ingredients, such as other active agents (such as anti-cancer agents and the active agents discussed below). In one embodiment, the pharmaceutical composition includes a therapeutically effective amount of one or more compounds of the present invention.

The invention further provides a pharmaceutical composition comprising compound A1 together with a pharmaceutically acceptable carrier.

The invention further provides a pharmaceutical composition comprising compound B together with a pharmaceutically acceptable carrier.

The invention further provides a pharmaceutical composition comprising compound B1 together with a pharmaceutically acceptable carrier.

In one embodiment, the invention provides a pharmaceutical composition comprising compound A1 or a pharmaceutically acceptable salt thereof, wherein compound A1 is present in excess of compound A2

In a further embodiment, the compound A1 is substantially free of compound A2.

In a further embodiment, the compound A1 exists in excess over compound A2 and has an enantiomeric excess (e.e.) of at least about 60%, 75%, 80%, 85%, 90%, 95%, 98% or 99%.

In another embodiment, the invention provides a pharmaceutical composition comprising compound B1 or a pharmaceutically acceptable salt thereof, wherein compound B1 is present in excess of compound B2

In a further embodiment, the compound B1 is substantially free of compound B2.

In a further embodiment, the compound B1 exists in excess over compound B2 and has an enantiomeric excess (e.e.) of at least about 60%, 75%, 80%, 85%, 90%, 95%, 98% or 99%.

Another embodiment is a method for preparing the 4-methylbenzenesulfonate (PTSA), sulphate (SA), hydrochloride (HCl), benzenesulfonate, maleate or camphor sulphonate salt of compound B or compound B1. The method can include converting compound B or B1, or a salt of it (other than the desired salt), to a 4-methylbenzenesulfonate, sulphate, hydrochloride, benzenesulfonate, maleate or camphor sulphonate salt of compound B or compound B1.

Another embodiment is a 4-methylbenzenesulfonate, sulphate, hydrochloride, benzenesulfonate, maleate or camphor sulphonate salt of compound B or compound B1 suitable for use in a pharmaceutical composition for the treatment of a PI3K associated disease, disorder or condition, e.g., a proliferative disease such as cancer.

The invention further provides a pharmaceutical composition comprising 4-methylbenzenesulfonate, sulphate, hydrochloride, benzenesulfonate, maleate or camphor sulphonate salt of Compound B of the present invention together with a pharmaceutically acceptable carrier. The pharmaceutical composition may further comprise one or more of additional active ingredients, such as other active agents (such as anti-cancer agents and the active agents discussed below). In one embodiment, the pharmaceutical composition includes a therapeutically effective amount of one or more compounds of the present invention.

The invention further provides a pharmaceutical composition comprising 4-methylbenzenesulfonate, sulphate, hydrochloride, benzenesulfonate, maleate or camphor sulphonate salt of Compound B together with a pharmaceutically acceptable carrier.

In one embodiment, the PTSA salt of compound B or compound B1 has an enantiomeric excess (e.e.) of at least about 60%, 75%, 80%, 85%, 90%, 95%, 98% or 99%.

In one embodiment, the SA salt of compound B or compound B1 has an enantiomeric excess (e.e.) of at least about 60%, 75%, 80%, 85%, 90%, 95%, 98% or 99%.

In one embodiment, the HCl salt of compound B or compound B1 has an enantiomeric excess (e.e.) of at least about 60%, 75%, 80%, 85%, 90%, 95%, 98% or 99%.

In one embodiment, the benzenesulfonate salt of compound B or compound B1 has an enantiomeric excess (e.e.) of at least about 60%, 75%, 80%, 85%, 90%, 95%, 98% or 99%.

In one embodiments, the maleate salt of compound B or compound B1 has an enantiomeric excess (e.e.) of at least about 60%, 75%, 80%, 85%, 90%, 95%, 98% or 99%.

In one embodiment, the camphor sulphonate salt of compound B or compound B1 has an enantiomeric excess (e.e.) of at least about 60%, 75%, 80%, 85%, 90%, 95%, 98% or 99%.

Another embodiment is a method of inhibiting PI3K delta in a patient by administering to a patient an effective amount of compound B or compound B1 of the present invention as a as PTSA salt.

Another embodiment is a method of inhibiting PI3K delta in a patient by administering to a patient an effective amount of at least one compound of the present invention.

Yet another embodiment is a method of treating, preventing, and/or inhibiting a PI3K protein kinase mediated disease, disorder or condition (such as cancer or other proliferative disease or disorder) in a patient by administering to the a patient an effective amount of at least one compound of the present invention.

Yet another embodiment is a method of treating a PI3K associated disease, disorder or condition in a patient by administering to the patient an effective amount of at least one compound of the present invention. In one embodiment, the amount of the compound administered is sufficient to treat a PI3K associated disease, disorder or condition by inhibition of PI3K delta.

Yet another embodiment of the present invention is a method for treating a proliferative disease by administering to a patient in need of such treatment an effective amount of at least one compound of the present invention. In one embodiment, the amount of the compound administered is sufficient to treat the proliferative disease by inhibition of PI3K delta.

Yet another embodiment of the present invention is a method for treating a proliferative disease by administering to a patient in need of such treatment an effective amount of at least one compound of the present invention, in combination (simultaneously or sequentially) with at least one other anti-cancer agent. In one embodiment, the amount of the compound administered is sufficient to treat (or facilitate treatment of) the proliferative disease by inhibition of PI3K delta.

Yet another embodiment is a method of treating a PI3K associated disease, disorder or condition in a patient, comprising administering to the patient a pharmaceutical composition comprising Compound A1, B or B1 or a pharmaceutically acceptable salt thereof, optionally admixed with at least one pharmaceutically acceptable excipient. In particular embodiments, the composition comprises a therapeutically effective amount of a compound of any of the foregoing embodiments of Compound A1, B or B1 or a pharmaceutically acceptable salt thereof for the treatment of PI3K associated disease, disorder or condition.

Specific embodiments provide a method of treating cancer in a patient, comprising administering to the patient a pharmaceutical composition comprising compound A1, B or B1 or a pharmaceutically acceptable salt thereof, optionally admixed with at least one pharmaceutically acceptable excipient. In particular embodiments, the composition comprises of a therapeutically effective amount of a compound of any of the foregoing embodiments of Compound A1, B or B1 or a pharmaceutically acceptable salt thereof for the treatment of cancer in a patient.

The compounds of the present invention are useful in the treatment of a variety of cancers, including, but not limited to, the following:

carcinoma, including that of the bladder, breast, colon, kidney, liver, lung (including small cell lung cancer), esophagus, gall bladder, uterus, ovary, testes, larynx, oral cavity, gastrointestinal tract (e.g., esophagus, stomach, pancreas), brain, cervix, thyroid, prostate, blood, and skin (including squamous cell carcinoma);

hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

The compounds of the present invention as modulators of apoptosis are useful in the treatment, prevention, and inhibition of cancer (including, but not limited to, those types mentioned herein above).

The compounds of the present invention are useful in the chemoprevention of cancer. Chemoprevention involves inhibiting the development of invasive cancer by blocking the initiating mutagenic event, blocking the progression of pre-malignant cells that have already suffered an insult, or inhibiting tumor relapse. The compounds are also useful in inhibiting tumor angiogenesis and metastasis. One embodiment of the invention is a method of inhibiting tumor angiogenesis or metastasis in a patient by administering an effective amount of one or more compounds of the present invention.

Another embodiment of the present invention is a method of treating an immune system-related disease (e.g., an autoimmune disease), a disease or disorder involving inflammation (e.g., asthma, chronic obstructive pulmonary disease, rheumatoid arthritis, inflammatory bowel disease, glomerulonephritis, neuroinflammatory diseases, multiple sclerosis, uveitis and disorders of the immune system), cancer or other proliferative disease, a hepatic disease or disorder, or a renal disease or disorder. The method includes administering an effective amount of one or more compounds of the present invention.

Examples of immune disorders which can be treated by the compounds of the present invention include, but are not limited to, psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, idiopathic pulmonary fibrosis (IPF) (or cryptogenic fibrosing alveolitis (CFA) or idiopathic fibrosing interstitial pneumonia), pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

Yet another embodiment is a method of treating leukemia in a patient by administering a therapeutically effective amount of a compound of the present invention. For example, the compounds of the present invention are effective for treating chronic lymphocytic leukemia (CLL), non-Hodgkin lymphoma (NHL), acute myeloid leukemia (AML), multiple myeloma (MM), small lymphocytic lymphoma (SLL), and indolent non-Hodgkin's lymphoma (I-NHL).

In the aforementioned methods of treatment, one or more additional active agents can be administered with the compounds of the present invention. For example, the compounds of the present invention are useful in combination (administered together or sequentially) with known anti-cancer treatments such as chemotherapy, radiation therapy, biological therapy, bone marrow transplantation, stem cell transplant or any other anticancer therapy or with one or more cytostatic, cytotoxic or anticancer agents or targeted therapy either alone or in combination, such as but not limited to, for example, DNA interactive agents, such as fludarabine, cisplatin, chlorambucil, bendamustine or doxorubicin; alkylating agents, such as cyclophosphamide; topoisomerase II inhibitors, such as etoposide; topoisomerase I inhibitors, such as CPT-11 or topotecan; tubulin interacting agents, such as paclitaxel, docetaxel or the epothilones (for example ixabepilone), either naturally occurring or synthetic; hormonal agents, such as tamoxifen; thymidilate synthase inhibitors, such as 5-fluorouracil; anti-metabolites, such as methotrexate; other tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2); CD20 monoclonal antibodies such as rituximab, ublixtumab (TGR-1101), ofatumumab (HuMax; Intracel), ocrelizumab, veltuzumab, GA101 (obinutuzumab), AME-133v (LY2469298, Applied Molecular Evolution), ocaratuzumab (Mentrik Biotech), PRO131921, tositumomab, hA20 (Immunomedics, Inc.), ibritumomab-tiuxetan, BLX-301 (Biolex Therapeutics), Reditux (Dr. Reddy's Laboratories), and PRO70769 (described in WO2004/056312); other B-cell targeting monoclonal antibodies such as belimumab, atacicept or fusion proteins such as blisibimod and BR3-Fc; other monoclonal antibodies such as alemtuzumab; CHOP (cyclophosphamide, doxorubicin, vincristine, prednisone); R-CHOP (rituximab-CHOP); hyperCV AD (hyperfractionated cyclophosphamide, vincristine, doxorubicin, dexamethasone, methotrexate, cytarabine); R-hyperCV AD (rituximab-hyperCV AD); FCM (fludarabine, cyclophosphamide, mitoxantrone); R-FCM (rituximab, fludarabine, cyclophosphamide, mitoxantrone); bortezomib and rituximab; temsirolimus and rituximab; temsirolimus and Velcade®; Iodine-131 tositumomab (Bexxar®) and CHOP-CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); FR (fludarabine, rituximab); and D.T. PACE (dexamethasone, thalidomide, cisplatin, adriamycin, cyclophosphamide, etoposide); and other protein kinase modulators.

The compounds of the present invention are also useful in combination (administered together or sequentially) with one or more steroidal anti-inflammatory drugs, non-steroidal anti-inflammatory drugs (NSAIDs) or immune selective anti-inflammatory derivatives (ImSAIDs).

BRIEF DESCRIPTION OF THE FIGURES

FIG. 1 is a bar graph of the percent apoptotic cells after treatment with compound B1 or Control in primary Multiple Myeloma patient cells as measured according to Assay 6a.

DETAILED DESCRIPTION OF THE INVENTION

Figure 1:
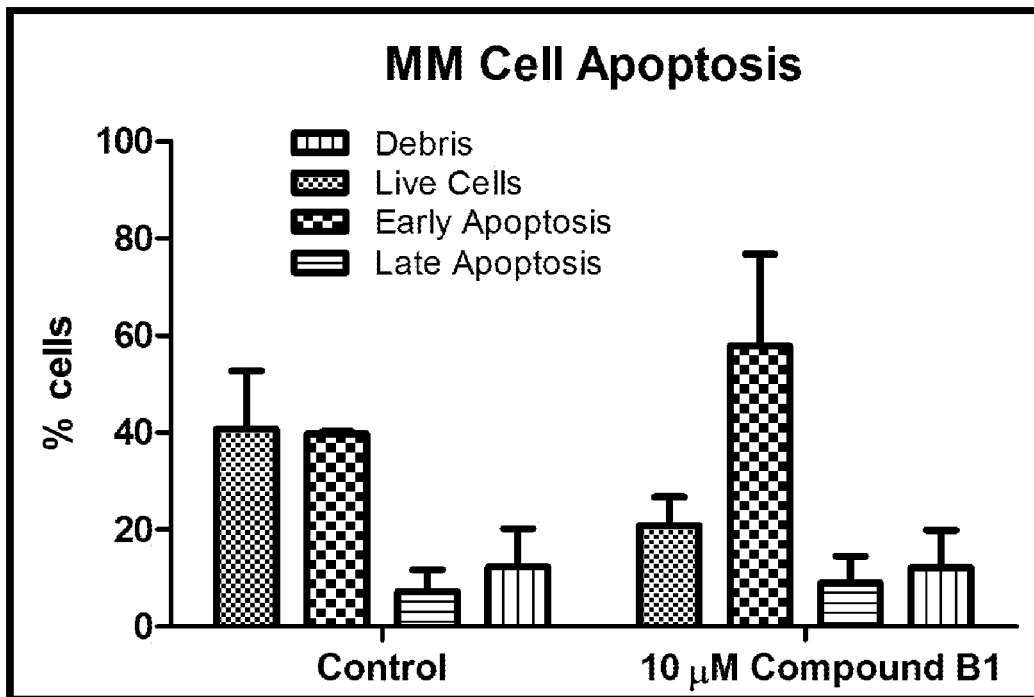

As used herein the following definitions shall apply unless otherwise indicated.

Certain of the compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. For instance, intermediate mixutures may include a mixture of isomers in a ratio of about 10:90, 13:87, 17:83, 20:80, or 22:78. Optically active (R)- and (S)-isomers can be prepared using chiral synthons or chiral reagents, or resolved using known techniques The term "prodrug" refers to a compound, which is an inactive precursor of a compound, converted into its active form in the body by normal metabolic processes. Prodrug design is discussed generally in Hardma, et al. (Eds.), *Goodman and Gilman's The Pharmacological Basis of Therapeutics*, 9th ed., pp. 11-16 (1996). A thorough discussion is provided in Higuchi, et al., *Prodrugs as Novel Delivery Systems*, Vol. 14, ASCD Symposium Series, and in Roche (ed.), *Bioreversible Carriers in Drug Design*, American Pharmaceutical Association and Pergamon Press (1987). To illustrate, prodrugs can be converted into a pharmacologically active form through hydrolysis of, for example, an ester or amide linkage, thereby introducing or exposing a functional group on the resultant product. The prodrugs can be designed to react with an endogenous compound to form a water-soluble conjugate that further enhances the pharmacological properties of the compound, for example, increased circulatory half-life. Alternatively, prodrugs can be designed to undergo covalent modification on a functional group with, for example, glucuronic acid, sulfate, glutathione, amino acids, or acetate. The resulting conjugate can be inactivated and excreted in the urine, or rendered more potent than the parent compound. High molecular weight conjugates also can be excreted into the bile, subjected to enzymatic cleavage, and released back into the circulation, thereby effectively increasing the biological half-life of the originally administered compound. Prodrugs of compounds A1, B, B1 and B2 are intended to be covered within the scope of this invention.

Additionally the instant invention also includes compounds which differ only in the presence of one or more isotopically enriched atoms, for example, replacement of hydrogen with deuterium or tritium, or the replacement of a carbon by $^{13}$C- or $^{14}$C-enriched carbon.

The compounds of the present invention may also contain unnatural proportions of atomic isotopes at one or more of atoms that constitute such compounds. For example, the compounds may be radiolabeled with radioactive isotopes, such as for example tritium ($^{3}$H), iodine-125 ($^{125}$I) or carbon-14 ($^{14}$C). All isotopic variations of the compounds of the present invention, whether radioactive or not, are encompassed within the scope of the present invention.

Pharmaceutically acceptable salts forming part of this invention include salts derived from inorganic bases such as Li, Na, K, Ca, Mg, Fe, Cu, Zn, and Mn; salts of organic bases such as N,N'-diacetylethylenediamine, glucamine, triethylamine, choline, hydroxide, dicyclohexylamine, metformin, benzylamine, trialkylamine, and thiamine; salts of chiral bases such as alkylphenylamine, glycinol, and phenyl glycinol; salts of natural amino acids such as glycine, alanine, valine, leucine, isoleucine, norleucine, tyrosine, cystine, cysteine, methionine, proline, hydroxy proline, histidine, omithine, lysine, arginine, and serine; quaternary ammonium salts of the compounds of invention with alkyl halides, alkyl sulphates such as MeI and $(Me)_2SO_4$; salts of non-natural amino acids such as D-isomers or substituted amino acids; salts of guanidine; and salts of substituted guanidine wherein the substituents are selected from nitro, amino, alkyl, alkenyl, alkynyl, ammonium or substituted ammonium salts and aluminum salts. Salts may include acid addition salts where appropriate which are sulphates, nitrates, phosphates, perchlorates, borates, hydrohalides, acetates, tartrates, maleates, citrates, fumarates, succinates, palmoates, methanesulphonates, benzoates, salicylates, benzenesulfonates, ascorbates, glycerophosphates, and ketoglutarates. In one embodiment, the salt is 4-methylbenzenesulfonate. In another embodiment, the salt is sulphate. In yet another embodiment, the salt is hydrochloride. In yet another embodiment, the salt is benzenesulfonate. In yet another embodiment, the salt is maleate. In yet another embodiment, the salt is camphor sulfonate.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range.

The term "comprising" (and related terms such as "comprise" or "comprises" or "having" or "including") includes, but is not limited to, those embodiments, for example, an embodiment of any composition of matter, composition, method, or process, or the like, that "consist of" or "consist essentially of" the described features.

The following abbreviations and terms have the indicated meanings throughout: PI3-K=Phosphoinositide 3-kinase; PI=phosphatidylinositol; DNA-PK=Deoxyribose Nucleic Acid Dependent Protein Kinase; PTEN=Phosphatase and Tensin homolog deleted on chromosome Ten; AIDS=Acquired Immuno Deficiency Syndrome; HIV=Human Immunodeficiency Virus; and MeI=Methyl Iodide.

Abbreviations used herein have their conventional meaning within the chemical and biological arts, unless otherwise indicated.

The term "cell proliferation" refers to a phenomenon by which the cell number has changed as a result of division. This term also encompasses cell growth by which the cell morphology has changed (e.g., increased in size) consistent with a proliferative signal.

The term "co-administration," "administered in combination with," and their grammatical equivalents, as used herein, encompasses administration of two or more agents to an animal so that both agents and/or their metabolites are present in the animal at the same time. Co-administration includes simultaneous administration in separate compositions, administration at different times in separate compositions, or administration in a composition in which both agents are present.

The term "effective amount" or "therapeutically effective amount" refers to that amount of a compound described herein that is sufficient to effect the intended application including, but not limited to, disease treatment. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, the terms "treatment" and "treating" refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as that term is used herein encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "subject" or "patient" refers to an animal, such as a mammal, for example a human. The methods described herein can be useful in both human therapeutics and veterinary applications. In some embodiments, the patient is a mammal, and in some embodiments, the patient is human. For veterinary purposes, the term "subject" and "patient" include, but are not limited to, farm animals including cows, sheep, pigs, horses, and goats; companion animals such as dogs and cats; exotic and/or zoo animals; laboratory animals including mice, rats, rabbits, guinea pigs, and hamsters; and poultry such as chickens, turkeys, ducks, and geese.

"Radiation therapy" refers to exposing a patient, using methods and compositions known to the practitioner, to radiation emitters such as alpha-particle emitting radionuclides (e.g., actinium and thorium radionuclides), low linear energy transfer (LET) radiation emitters (i.e. beta emitters), conversion electron emitters (e.g. strontium-89 and samarium -153-EDTMP), or high-energy radiation, including without limitation x-rays, gamma rays, and neutrons.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

The term "selective inhibition" or "selectively inhibit" as applied to a biologically active agent refers to the agent's ability to selectively reduce the target signaling activity as compared to off-target signaling activity, via direct or indirect interaction with the target.

As used herein, the term "PI3-kinase δ selective inhibitor" generally refers to a compound that inhibits the activity of the PI3-kinase δ isozyme more effectively than other isozymes of the PI3K family (alpha, beta, and gamma). For instance, the PI3-kinase δ selective inhibitor may refer to a compound that exhibits a 50% inhibitory concentration (IC50) with respect to the delta type I PI3-kinase that is at least 10-fold at least 20-fold, at least 50-fold, at least 100-fold, or lower, than the inhibitor's IC50 with respect to the rest of the other type 1 PI3-kinases (i.e., alpha, beta, and gamma).

Inhibition of PI3-kinase δ may be of therapeutic benefit in the treatment of various conditions, e.g., conditions characterized by an inflammatory response including but not limited to autoimmune diseases, allergic diseases, and arthritic diseases. Importantly, inhibition of PI3-kinase δ function does not appear to affect biological functions such as viability and fertility.

"Inflammatory response" as used herein is characterized by redness, heat, swelling and pain (i.e., inflammation) and typically involves tissue injury or destruction. An inflammatory response is usually a localized, protective response elicited by injury or destruction of tissues, which serves to destroy, dilute or wall off (sequester) both the injurious agent and the injured tissue. Inflammatory responses are notably associated with the influx of leukocytes and/or leukocyte (e.g., neutrophil) chemotaxis. Inflammatory responses may result from infection with pathogenic organisms and viruses, noninfectious means such as trauma or reperfusion following myocardial infarction or stroke, immune responses to foreign antigens, and autoimmune diseases. Inflammatory responses amenable to treatment with the methods and compounds according to the invention encompass conditions associated with reactions of the specific defense system as well as conditions associated with reactions of the non-specific defense system.

The therapeutic methods of the invention include methods for the treatment of conditions associated with inflammatory cell activation. "Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatibility antigens or cell adhesion molecules) in inflammatory cells (including, but not limited to, monocytes, macrophages, T lymphocytes, B lymphocytes, granulocytes (polymorphonuclear leukocytes including neutrophils, basophils, and eosinophils) mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory condition.

"Autoimmune disease" as used herein refers to any group of disorders in which tissue injury is associated with humoral or cell-mediated responses to the body's own constituents.

"Transplant rejection" as used herein refers to an immune response directed against grafted tissue (including organs or cells (e.g., bone marrow), characterized by a loss of function of the grafted and surrounding tissues, pain, swelling, leukocytosis, and thrombocytopenia).

"Allergic disease" as used herein refers to any symptoms, tissue damage, or loss of tissue function resulting from allergy.

"Arthritic disease" as used herein refers to any disease that is characterized by inflammatory lesions of the joints attributable to a variety of etiologies.

"Dermatitis" as used herein refers to any of a large family of diseases of the skin that are characterized by inflammation of the skin attributable to a variety of etiologies.

The compounds of the present invention can be prepared by the methods described in International Publication No. WO 2011/055215 and PCT Application No. PCT/IB2013/053544, filed May 3, 2013, both of which are hereby incorporated by reference. Compound A can be prepared as described in Example 158 of International Publication No. WO 2011/055215.

Pharmaceutical Compositions

The invention provides a pharmaceutical composition comprising one or more compounds of the present invention and one or more pharmaceutically acceptable carriers or excipients. In one embodiment, the pharmaceutical composition includes a therapeutically effective amount of a compound of the present invention. The pharmaceutical composition may include one or more additional active ingredients as described herein.

The pharmaceutical carriers and/or excipients may be selected from diluents, fillers, salts, disintegrants, binders, lubricants, glidants, wetting agents, controlled release matrices, colorants, flavorings, buffers, stabilizers, solubilizers, and combinations thereof.

The pharmaceutical compositions of the present invention can be administered alone or in combination with one or more other active agents. Where desired, the subject compounds and other agent(s) may be mixed into a preparation or both components may be formulated into separate preparations to use them in combination separately or at the same time.

The compounds and pharmaceutical compositions of the present invention can be administered by any route that enables delivery of the compounds to the site of action, such as orally, intranasally, topically (e.g., transdermally), intraduodenally, parenterally (including intravenously, intraarterially, intramuscularally, intravascularally, intraperitoneally or by injection or infusion), intradermally, by intramammary, intrathecally, intraocularly, retrobulbarly, intrapulmonary (e.g., aerosolized drugs) or subcutaneously (including depot administration for long term release e.g., embedded-under the-splenic capsule, brain, or in the cornea), sublingually, anally, rectally, vaginally, or by surgical implantation (e.g., embedded under the splenic capsule, brain, or in the cornea).

The compositions can be administered in solid, semi-solid, liquid or gaseous form, or may be in dried powder, such as lyophilized form. The pharmaceutical compositions can be packaged in forms convenient for delivery, including, for example, solid dosage forms such as capsules, sachets, cachets, gelatins, papers, tablets, suppositories, pellets, pills, troches, and lozenges. The type of packaging will generally depend on the desired route of administration. Implantable sustained release formulations are also contemplated, as are transdermal formulations.

The amount of the compound to be administered is dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. An effective amount of a compound of the invention may be administered in either single or multiple doses (e.g., twice or three times a day).

The compounds of the present invention may be used in combination with one or more of anti-cancer agents (e.g., chemotherapeutic agents), therapeutic antibodies, and radiation treatment.

The compounds of the invention may be formulated or administered in conjunction with other agents that act to relieve the symptoms of inflammatory conditions such as encephalomyelitis, asthma, and the other diseases described herein. These agents include non-steroidal anti-inflammatory drugs (NSAIDs).

Preparations of various pharmaceutical compositions are known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 2003; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999), all of which are incorporated by reference herein in their entirety.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

In one embodiment, Compound A1 or a pharmaceutically acceptable salt thereof is administered at a dose selected to produce a concentration of compound in the blood between about 20 to 5,000 ng/mL, and maintaining such concentration during a period of about 6 to 24 hours following administration. In another particular embodiment, the dose size and frequency are selected to achieve a concentration of compound in the blood that is between about 50 to 2,500 ng/mL and maintain that concentration during a period of about 6 to 24 hours from the time of administration. In some embodiments, the dose size and frequency are selected to achieve a concentration of compound in the blood that is between about 100 to 1,500 ng/mL following administration. In some embodiments, the dose size and frequency are selected to achieve a concentration of compound in the blood that is between about 100 to 750 ng/mL over a period of about 6 to 24 hours from the time of administration. In further embodiments, the dose size and frequency is selected to achieve a $C_{max}$, plasma level of Compound A1 that is at least about 300 ng/mL and does not exceed about 10,000 ng/mL In one embodiment, Compound B1 or a pharmaceutically acceptable salt thereof is administered at a dose selected to produce a concentration of compound in the blood between about 20 to 5,000 ng/mL, and maintaining such concentration during a period of about 6 to 24 hours following administration. In another particular embodiment, the dose size and frequency are selected to achieve a concentration of compound in the blood that is between about 50 to 2,500 ng/mL and maintain that concentration during a period of about 6 to 24 hours from the time of administration. In some embodiments, the dose size and frequency are selected to achieve a concentration of compound in the blood that is between about 100 to 1,500 ng/mL following administration. In some embodiments, the dose size and frequency are selected to achieve a concentration of compound in the blood that is between about 100 to 750 ng/mL over a period of about 6 to 24 hours from the time of administration. In further embodiments, the dose size and frequency is selected to achieve a $C_{max}$, plasma level of Compound B1 that is at least about 300 ng/mL and does not exceed about 10,000 ng/mL Method of Treatment The invention also provides methods of using the compounds or pharmaceutical compositions of the present invention to treat disease conditions, including but not limited to diseases associated with malfunctioning of one or more types of PI3 kinase. A detailed description of conditions and disorders mediated by PI3 δ kinase activity is set forth in WO 2001/81346, U.S. 2005/043239, WO 2010/123931, WO 2010/111432 and WO 2010/057048, all of which are incorporated herein by reference in their entireties for all purposes.

The treatment methods provided herein comprise administering to the subject a therapeutically effective amount of a compound of the invention. In one embodiment, the present invention provides a method of treating an inflammation disorder, including autoimmune diseases in a mammal. The method comprises administering to said mammal a therapeutically effective amount of a compound of the present invention.

The disorders, diseases, or conditions treatable with a compound provided herein, include, but are not limited to,
  inflammatory or allergic diseases, including systemic anaphylaxis and hypersensitivity disorders, atopic dermatitis, urticaria, drug allergies, insect sting allergies, food allergies (including celiac disease and the like), anaphylaxis, serum sickness, drug reactions, insect venom allergies, hypersensitivity pneumonitis, angioedema, erythema multiforme, Stevens-Johnson syndrome, atopic keratoconjunctivitis, venereal keratoconjunctivitis, giant papillary conjunctivitis, and mastocytosis;
  inflammatory bowel diseases, including Crohn's disease, ulcerative colitis, ileitis,enteritis, and necrotizing enterocolitis;
  vasculitis, and Behcet's syndrome;
  psoriasis and inflammatory dermatoses, including dermatitis, eczema, allergic contact dermatitis, viral cutaneous pathologies including those derived from human papillomavirus, HIV or RLV infection, bacterial, flugal, and other parasital cutaneous pathologies, and cutaneous lupus erythematosus;
  asthma and respiratory allergic diseases, including allergic asthma, exercise induced asthma, allergic rhinitis, otitis media, hypersensitivity lung diseases, chronic obstructive pulmonary disease and other respiratory problems;
  autoimmune diseases and inflammatory conditions, including but are not limited to, lupus erythematosus, systemic lupus erythematosus (SLE), multiple sclerosis, polyarthritis, primary biliary cirrhosis, psoriasis, rheumatoid arthritis, psoriatic arthritis, gouty arthritis, spondylitis, reactive arthritis, chronic or acute glomerulonephritis, lupus nephritis, Reiter's syndrome, Takayasu's arteritis, temporal arteritis (also known as "giant cell arteritis"), autoimmune pulmonary inflammation, autoimmune thyroiditis, autoimmune inflammatory eye disease, vitiligo, and vulvodynia. Other disorders include bone-resorption disorders and thromobsis;

cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood, and lymphatic system; and pulmonary or respiratory conditions including but not limited to asthma, chronic bronchitis, allergic rhinitis, adult respiratory distress syndrome (ARDS), severe acute respiratory syndrome (SARS), chronic pulmonary inflammatory diseases (e.g., chronic obstructive pulmonary disease), silicosis, pulmonary sarcoidosis, pleurisy, alveolitis, vasculitis, pneumonia, bronchiectasis, hereditary emphysema, and pulmonary oxygen toxicity.

In certain embodiments, the cancer or cancers treatable with the methods provided herein includes, but is or are not limited to, leukemias, including, but not limited to, acute leukemia, acute lymphocytic leukemia, acute myelocytic leukemias such as myeloblasts, promyelocyte, myelomonocytic, monocytic, erythroleukemia leukemias and myelodysplastic syndrome or a symptom thereof (such as anemia, thrombocytopenia, neutropenia, bicytopenia or pancytopenia), refractory anemia (RA), RA with ringed sideroblasts (RARS), RA with excess blasts (RAEB), RAEB in transformation (RAEB-T), preleukemia, and chronic myelomonocytic leukemia (CMML);

chronic leukemias, including, but not limited to, chronic myelocytic (granulocytic) leukemia, chronic lymphocytic leukemia, and hairy cell leukemia;

polycythemia vera;

lymphomas, including, but not limited to, Hodgkin's disease and non-Hodgkin's disease;

multiple myelomas, including, but not limited to, smoldering multiple myeloma, nonsecretory myeloma, osteosclerotic myeloma, plasma cell leukemia, solitary plasmacytoma, and extramedullary plasmacytoma;

Waldenstrom's macroglobulinemia;

monoclonal gammopathy of undetermined significance;

benign monoclonal gammopathy;

heavy chain disease;

bone and connective tissue sarcomas, including, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, and synovial sarcoma;

brain tumors, including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma;

breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer;

adrenal cancer, including, but not limited to, pheochromocytom and adrenocortical carcinoma;

thyroid cancer, including, but not limited to, papillary or follicular thyroid cancer, medullary thyroid cancer, and anaplastic thyroid cancer;

pancreatic cancer, including, but not limited to,insulinoma, gastrinoma, glucagonoma, vipoma, somatostatin-secreting tumor, and carcinoid or islet cell tumor;

pituitary cancer, including, but limited to, Cushing's disease, prolactin-secreting tumor, acromegaly, and diabetes insipidus;

eye cancer, including, but not limited, to ocular melanoma such as iris melanoma, choroidal melanoma, and ciliary body melanoma, and retinoblastoma;

vaginal cancer, including, but not limited to, squamous cell carcinoma, adenocarcinoma, and melanoma;

vulvar cancer, including, but not limited to, squamous cell carcinoma, melanoma, adenocarcinoma, basal cell carcinoma, sarcoma, and Paget's disease;

cervical cancers, including, but not limited to, squamous cell carcinoma, and adenocarcinoma;

uterine cancer, including, but not limited to, endometrial carcinoma and uterine sarcoma;

ovarian cancer, including, but not limited to, ovarian epithelial carcinoma, borderline tumor, germ cell tumor, and stromal tumor;

esophageal cancer, including, but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma;

stomach cancer, including, but not limited to, adenocarcinoma, fungating (polypoid), ulcerating, superficial spreading, diffusely spreading, malignant lymphoma, liposarcoma, fibrosarcoma, and carcinosarcoma;

colon cancer;

rectal cancer;

liver cancer, including, but not limited to, hepatocellular carcinoma and hepatoblastoma;

gallbladder cancer, including, but not limited to, adenocarcinoma;

cholangiocarcinomas, including, but not limited to, pappillary, nodular, and diffuse;

lung cancer, including, but not limited to, non-small cell lung cancer, squamous cell carcinoma (epidermoid carcinoma), adenocarcinoma, large-cell carcinoma, and small-cell lung cancer;

testicular cancer, including, but not limited to, germinal tumor, seminoma, anaplastic, classic (typical), spermatocytic, nonseminoma, embryonal carcinoma, teratoma carcinoma, and choriocarcinoma (yolk-sac tumor);

prostate cancer, including, but not limited to, adenocarcinoma, leiomyosarcoma, and rhabdomyosarcoma;

penal cancer;

oral cancer, including, but not limited to, squamous cell carcinoma;

basal cancer;

salivary gland cancer, including, but not limited to, adenocarcinoma, mucoepidermoid carcinoma, and adenoidcystic carcinoma;

pharynx cancer, including, but not limited to, squamous cell cancer and verrucous;

skin cancer, including, but not limited to, basal cell carcinoma, squamous cell carcinoma and melanoma, superficial spreading melanoma, nodular melanoma, lentigo malignant melanoma, and acral lentiginous melanoma;

kidney cancer, including, but not limited to, renal cell cancer, adenocarcinoma, hypernephroma, fibrosarcoma, and transitional cell cancer (renal pelvis and/or uterer);

Wilms' tumor;

bladder cancer, including, but not limited to, transitional cell carcinoma, squamous cell cancer, adenocarcinoma, and carcinosarcoma; and other cancer, including, not limited to, myxosarcoma, osteogenic sarcoma, endotheliosarcoma, lymphangio-endotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, and papillary adenocarcinomas See Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America.

It will be appreciated that the treatment methods of the invention are useful in the fields of human medicine and veterinary medicine. Thus, the individual to be treated may be a mammal, preferably human, or other animals. For veterinary purposes, individuals include but are not limited to farm animals including cows, sheep, pigs, horses, and goats; companion animals such as dogs and cats; exotic and/or zoo animals; laboratory animals including mice, rats, rabbits, guinea pigs, and hamsters; and poultry such as chickens, turkeys, ducks, and geese.

The invention also relates to a method of treating a hyperproliferative disorder in a subject that comprises administering to said mammal a therapeutically effective amount of a compound of the present invention or a pharmaceutically acceptable salt thereof. In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g. Lymphoma and Kaposi's Sarcoma) or viral-induced cancer. In some embodiments, said method relates to the treatment of a non-cancerous hyperproliferative disorder such as benign hyperplasia of the skin (e. g., psoriasis), restenosis, or prostate (e.g., benign prostatic hypertrophy (BPH)).

EXAMPLES

The examples and preparations provided below further illustrate and exemplify the methods of preparing compounds of the invention. It is to be understood that the scope of the present invention is not limited in any way by the scope of the following examples and preparations. In the following examples molecules with a single chiral center, unless otherwise noted, exist as a racemic mixture. Single enantiomers may be obtained by methods known to those skilled in the art.

Unless otherwise mentioned, work-up refers to distribution of the reaction mixture between the aqueous and organic phases indicated within parentheses, separation and drying over $Na_2SO_4$ of the organic layer and evaporating the solvent to give a residue. Unless otherwise stated, purification implies column chromatography using silica gel as the stationary phase and a mixture of petroleum ether (boiling at 60-80° C.) and ethyl acetate or dichloromethane and methanol of suitable polarity as the mobile phases. RT refers to ambient temperature (25-28° C.).

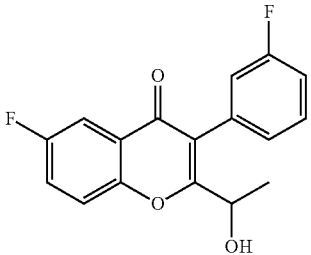

Intermediate 1

Intermediate 1: 6-fluoro-3-(3-fluorophenyl)-2-(1-hydroxyethyl)-4H-chromen-4-one: To a solution of 2-(1-bromoethyl)-6-fluoro-3-(3-fluorophenyl)-4H-chromen-4-one (15.0 g, 40.84 mmol) in DMSO (150 ml), n-butanol (7.5 ml) was added and heated to 120° C. for 3 h. The reaction mixture was cooled to RT, quenched with water and extracted with ethyl acetate. The organic layer was dried over sodium sulphate and concentrated under reduced pressure. The crude product was purified by column chromatography with ethyl acetate:petroleum ether to afford the title compound as an off-white solid (7.90 g, 64%). $^1$H-NMR (δ ppm, $CDCl_3$, 400 MHz): 7.85 (dd, J=8.1, 3 Hz, 1H), 7.54 (dd, J=9.2, 4.2 Hz, 1H), 7.47-7.37 (m, 2H), 7.15-6.98 (m, 3H), 4.74 (quintet, J=6.8 Hz, 1H), 2.23 (d, J=7.4 Hz, 1H), 1.54 (d, J=6.6 Hz, 3H).

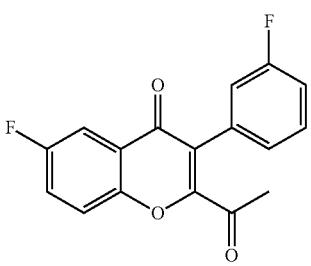

Intermediate 2

Intermediate 2: 2-acetyl-6-fluoro-3-(3-fluorophenyl)-4H-chromen-4-one: DMSO (5.60 ml, 79.14 mmol) was added to dichloromethane (40 ml) cooled to −78° C., followed by oxalyl chloride (3.40 ml, 39.57 mmol). After 10 min intermediate 1 (6.00 g, 19.78 mmol) in dichloromethane (54 ml) was added dropwise and stirred for 20 min. Triethylamine (12 ml) was added and stirred for 1 h. The reaction mixture was quenched with water and extracted with dichloromethane. The organic layer was dried over sodium sulphate and concentrated under reduced pressure. The crude product was purified by column chromatography with ethyl acetate: petroleum ether to afford the title compound as a yellow solid (4.2 g, 71%) which was used as such in the next step.

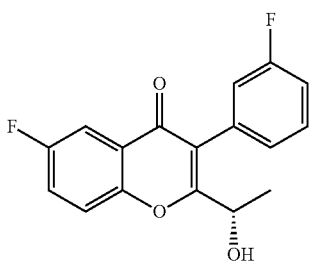

Intermediate 3

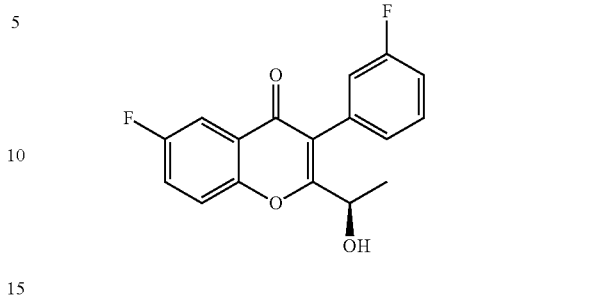

Intermediate 5

Intermediate 3: (S)-6-fluoro-3-(3-fluorophenyl)-2(1-hydroxyethyl)-4H-chromen-4-one: To intermediate 2 (2.00 g, 6.66 mmol), R-Alpine borane (0.5M in THF, 20 ml) was added and heated to 60° C. for 20 h. The reaction mixture quenched with aq. 2N HCl, and extracted with ethyl acetate. The organic layer was dried over sodium sulphate and concentrated under reduced pressure. The crude product was purified by column chromatography with ethyl acetate:petroleum ether to afford the title compound as an off-white solid (1.51 g, 75%). Enantiomeric excess: 94.2%, enriched in the fast eluting isomer (retention time: 8.78 min) as determined by HPLC on a chiralpak AD-H column.

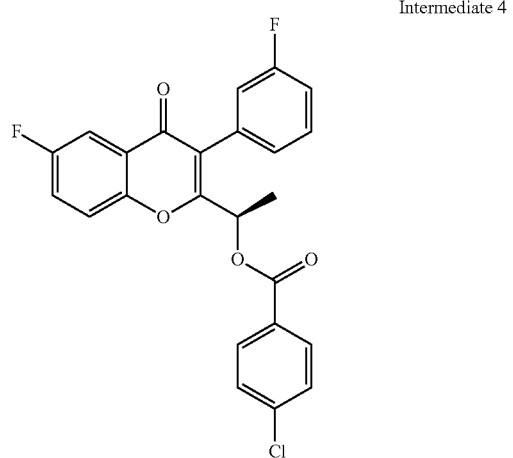 [SMILES: C[C@@H](OC(=O)c1ccc(Cl)cc1)c1oc2ccc(F)cc2c(=O)c1-c1cccc(F)c1]

Intermediate 4

Intermediate 4: (R)-1-(6-fluoro-3-(3-fluorophenyl)-4-oxo-4H-chromen-2-yl)ethyl 4-chlorobenzoate: To a solution of intermediate 3 (1.45 g, 4.78 mmol) in THF (15 ml), 4-chlorobenzoic acid (0.748 g, 4.78 mmol) and triphenylphosphine (1.88 g, 7.17 mmol) were added and heated to 45° C. followed by diisopropylazodicarboxylate (1.4 ml, 7.17 mmol). After 1 h, the reaction mixture was concentrated and the residue was purified by column chromatography with ethyl acetate:petroleum ether to afford the title compound as an off-white solid (1.81 g, 86%) which was used without purification in the next step.

Method A

Intermediate 5: (R)-6-fluoro-3-(3-fluorophenyl)-2-(1-hydroxyethyl)-4H-chromen-4-one: To intermediate 4 (1.75 g, 3.96 mmol) in methanol (17 ml) cooled to 10° C., potassium carbonate (0.273 g, 1.98 mmol) was added and stirred for 30 min. The reaction mixture was concentrated, acidified with 2N HCl solution, extracted with ethyl acetate, dried over sodium sulphate and concentrated under reduced pressure. The crude product was purified by column chromatography with ethyl acetate:petroleum ether to afford the title compound as a yellow solid (1.05 g, 87%). Enantiomeric excess: 93.6%, enriched in the late eluting isomer (retention time: 11.12 min) as determined by HPLC on a chiralpak AD-H column.

Method B:

Step-1: (R)-2-(1-(benzyloxy)ethyl)-6-fluoro-3-(3-fluorophenyl)-4H-chromen-4-one: To 1-(5-fluoro-2-hydroxyphenyl)-2-(3-fluorophenyl)ethanone (11.00 g, 44.31 mmol) in dichloromethane, HATU (33.7 g, 88.63 mmol) and R-(+)2-benzyloxypropionic acid (9.58 g, 53.17 mmol) were added and stirred for 10 min. Triethylamine (66.7 ml, 0.47 mol) was added dropwise and stirred at RT for 24 h. The reaction mixture was quenched with water, extracted with dichloromethane, dried over sodium sulphate and concentrated under reduced pressure. The crude product was purified by column chromatography with ethyl acetate:petroleum ether to afford the title compound as a yellow solid (10.5 g, 60%). $^1$H-NMR (δ ppm, CDCl$_3$, 400 MHz): 7.85 (dd, J=8.1, 3 Hz, 1H), 7.58 (dd, J=9.1, 4.1 Hz, 1H), 7.47-7.39 (m, 1H), 7.39-7.34 (m, 1H), 7.28-7.20 (m, 3H), 7.20-7.14 (m, 2H), 7.16-7.07 (m, 1H), 6.99-6.89 (m, 2H), 4.50-4.31 (m, 3H), 1.56 (d, J=6.4 Hz, 3H).

Step-2: (R)-2-(1-(benzyloxy)ethyl)-6-fluoro-3-(3-fluorophenyl)-4H-chromen-4-one (10.5 g, 26.69 mmol) in dichloromethane (110 ml) cooled to 0° C., aluminium chloride (5.35 g, 40.03 mmol) was added portionwise and stirred at RT for 6 h. The reaction mixture was quenched with 2N HCl solution, extracted with dichloromethane, dried over sodium sulphate and concentrated under reduced pressure. The crude product was purified by column chromatography with ethyl acetate:petroleum ether to afford the desired intermediate as a yellow solid (6.1 g, 76%). Enantiomeric excess: 97.7%, enriched in the late eluting isomer (retention time: 11.12 min) as determined by HPLC on a chiralpak AD-H column.

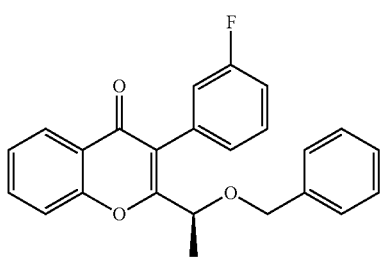

Intermediate 6

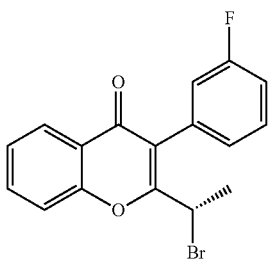

and

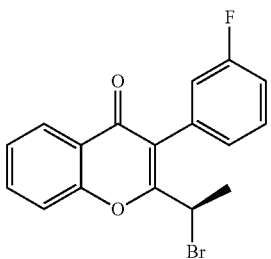

Intermediate 7a and 7b

Intermediate 6: (R)-2-(1-(benzyloxy)ethyl)-3-(3-fluorophenyl)-4H-chromen-4-one: To 2-(3-fluorophenyl)-1-(2-hydroxyphenyl)ethanone (10.0 g, 43.43 mmol) in dichloromethane (75 ml), HATU (33.0 g, 86.86 mmol) and R-(+) 2-benzyloxypropionic acid (9.39 g, 52.12 mmol) were added and stirred for 10 min. Triethylamine (65.4 ml, 0.469 mol) was added dropwise and stirred at RT for 24 h. The reaction mixture was quenched with water, extracted with dichloromethane, dried over sodium sulphate and concentrated under reduced pressure. The crude product was purified by column chromatography with ethyl acetate:petroleum ether to afford the title compound as a off-white solid (9.0 g, 55%). $^1$H-NMR (δ ppm, CDCl$_3$, 400 MHz): 8.23 (dd, J=7.9, 1.2 Hz, 1H), 7.74-7.70 (m, 1H), 7.58 (d, J=8.3 Hz, 1H), 7.43 (t, J=7.2 Hz, 1H), 7.37 (q, J=7.2 Hz, 1H), 7.29-7.15 (m, 5H), 7.09 (dt, J=8.6, 1.7 Hz, 1H), 7.00-6.90 (m, 2H), 4.51-4.35 (m, 3H), 1.57 (d, J=6.4 Hz, 3H).

Intermediate 7a and 7b: (S)-2-(1-bromoethyl)-3-(3-fluorophenyl)-4H-chromen-4-one and (R)-2-(1-bromoethyl)-3-(3-fluorophenyl)-4H-chromen-4-one: The two enantiomerically pure isomers were separated by preparative SFC conditions from 2-(1-bromoethyl)-3-(3-fluorophenyl)-4H-chromen-4-one (10 g) using CO$_2$:MeOH and analysed on a XBridge C18 column (50×4.6 mm; 3.5 μm) using water (10 mM ammonium bicarbonate):acetonitrile (gradient: 5%-95% acetonitrile in 1.2 min) as the mobile phase at a flow rate of 2.0 ml/min.

Intermediate 7a: Off-white solid (3.80 g). e.e. 100%. Rt: 1.79 min Mass: 348.9 (M$^+$+1).

Intermediate 7b: Off-white solid (3.8 g). e.e. 100%. Rt: 1.79 min Mass: 348.9 (M$^+$+1).

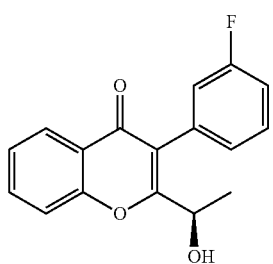

Intermediate 7

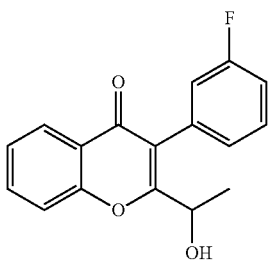

Intermediate 8

Intermediate 7: (R)-3-(3-fluorophenyl)-2-(1-hydroxyethyl)-4H-chromen-4-one: To intermediate 6 (5.0 g, 13.35 mmol) in dichloromethane (50 ml) cooled to −78° C., boron tribromide (1M in dichloromethane, 36.5 ml, 0.145 mmol) was added dropwise and stirred for 1 h. The reaction mixture was quenched with 2N HCl solution, extracted with dichloromethane, dried over sodium sulphate and concentrated under reduced pressure. The crude product was purified by column chromatography with ethyl acetate: petroleum ether to afford intermediate II as an off-white solid (3.05 g, 80%). $^1$H-NMR (δ ppm, CDCl$_3$, 400 MHz): 8.24 (dd, J=7.9, 1.5 Hz, 1H), 7.73 (m, 1H), 7.54 (d, J=8.1 Hz, 1H), 7.44 (m, 2H), 7.13-7.01 (m, 3H), 4.71 (q, J=6.6 Hz, 1H), 1.56 (d, J =6.5 Hz, 3H). Mass: 284.9(M$^+$). Purity: 99.73%. $[\alpha]^{25}_D$ −0.605 (c=1, CHCl$_3$). Enantiomeric excess: 95.2%, enriched in the late eluting isomer (retention time: 10.19 min) as determined by HPLC on a chiralpak AD-H column.

Intermediate 8: 3-(3-fluorophenyl)-2-(1-hydroxyethyl)-4H-chromen-4-one: To a solution of 2-(1-bromoethyl)-3-(3-fluorophenyl)-4H-chromen-4-one (30 g, 86.51 mmol) in DMSO (300 ml), n-butanol (15 ml) was added and heated to 120° C. for 3 h. The reaction mixture was cooled to RT, quenched with water and extracted with ethyl acetate. The organic layer was dried over sodium sulphate and concentrated under reduced pressure. The crude product was purified by column chromatography with ethyl acetate:petroleum ether to afford the title compound as a off-white solid (16 g, 64%) which was used as such in next step.

Intermediate 9

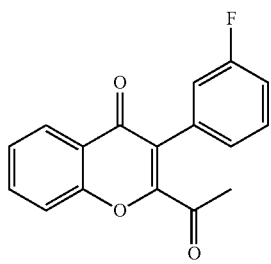

Intermediate 9: 2-acetyl-3-(3-fluorophenyl)-4H-chromen-4-one: DMSO (16.0 ml, 227 mmol) was added to dichloromethane (200 ml) cooled to −78° C., followed by oxalyl chloride (9.80 ml, 113.5 mmol). After 10 min. intermediate 8 (16.2 g, 56.79 mmol) in dichloromethane (54 ml) was added dropwise and stirred for 20 min. Triethylamine (32 ml) was added and stirred for 1 h. The reaction mixture was quenched with water and extracted with dichloromethane. The organic layer was dried over sodium sulphate and concentrated under reduced pressure. The crude product was purified by column chromatography with ethyl acetate: petroleum ether to afford the title compound as a yellow solid (8.2 g, 51%). $^1$H-NMR (δ ppm, CDCl$_3$, 400 MHz): 8.26 (dd, J=8.0, 1.5 Hz, 1H), 7.79 (m, 1H), 7.58 (d, J=8.3 Hz, 1H), 7.50 (dt, J=8.0,0.8 Hz, 1H), 7.41 (m, 1H), 7.15 (m, 1H), 7.01 (m, 2H), 2.37 (s, 3H).

Intermediate 10

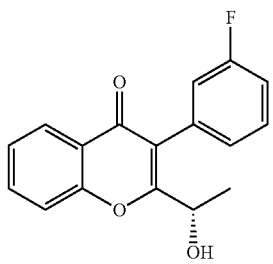

Intermediate 10: (S)-3-(3-fluorophenyl)-2-(1-hydroxyethyl)-4H-chromen-4-one: To intermediate 8 (1.00 g, 3.53 mmol) in THF (2 ml), R-Alpine borane (0.5M in THF, 10 ml) was added and heated to 60° C. for 20 h. The reaction mixture quenched with aq. 2N HCl, and extracted with ethyl acetate. The organic layer was dried over sodium sulphate and concentrated under reduced pressure. The crude product was purified by column chromatography with ethyl acetate: petroleum ether to afford the title compound as a off-white solid (0.400 g, 40%). Enantiomeric excess: 94.8%, enriched in the fast eluting isomer (retention time: 8.71 min.) as determined by HPLC on a chiralpak AD-H column.

Intermediate 11

Intermediate 11: 4-bromo-2-fluoro-1-isopropoxybenzene: To a solution of 4-bromo-2-fluorophenol (10 g, 52.35 mmol) in THF (100 ml), isopropyl alcohol (4.8 ml, 62.62 mmol) and triphenylphosphine (20.6 g, 78.52 mmol) were added and heated to 45° C. followed by diisopropylazodicarboxylate (15.4 ml, 7852 mmol). The mixture was refluxed for 1 h, concentrated and the residue was purified by column chromatography with ethyl acetate:petroleum ether to afford the title compound as a colourless liquid (13.1g, 99%) which was used without purification in the next step.

Intermediate 12

Intermediate 12: 2-(3-fluoro-4-isopropoxyphenyl)-4,4,5,5-tetramethyl-1,3,2-dioxaborolane: Potassium acetate (10.52 g, 107.2 mmol) and bis(pinacolato)diboron (15 g, 58.96 mmol) were added to a solution of intermediate 11 (10.52 g, 107.2 mmol) in dioxane (125 ml), and the solution was degas sed for 30 min. [1,1'-Bis(diphenylphosphino) ferrocene]dichloro palladium(II). CH$_2$Cl$_2$ (4.4 g, 5.36 mmol) was added under nitrogen atmosphere and heated to 80° C. After 12 h, the reaction mixture was filtered through celite and concentrated. The crude product was purified by column chromatography with ethyl acetate:petroleum ether to afford the title compound as a yellow oil (13.9 g, 99%) which was used without purification in the next step.

Intermediate 13

Intermediate 13: 3-(3-fluoro-4-isopropoxyphenyl)-1H-pyrazolo[3,4-d]pyrimidin-4-amine: To a solution of 3-iodo-1H-pyrazolo[3,4-d]pyrimidin-4-amine (11.0 g, 42.14 mmol) in DMF 110 ml), ethanol (55 ml) and water (55 ml), intermediate 12 (23.4 g, 84.28 mmol) and sodium carbonate (13.3 g, 126.42 mmol) were added and degassed for 30 min. Tetrakis(triphenylphosphine)palladium(0) (2.4 g, 2.10 mmol) was added under nitrogen atmosphere and heated to 80° C. After 12 h, the reaction mixture was filtered though celite, concentrated and extracted with ethyl acetate. The organic layer was dried over sodium sulphate and concentrated under reduced pressure. The crude product was triturated with diethyl ether, filtered and dried under vacuum to afford the title compound as light brown solid (3.2 g, 26% yield) which is used as such for the next step.

Example A 2-(1-(4-amino-3-(3-fluoro-4-isopropoxyphenyl)-1H-pyrazolo[3,4-d]pyrimidin-1-yl)ethyl)-3-(3-fluorophenyl)-4H-chromen-4-one The title compound is prepared as described in Example 158 of International Publication No. WO 2011/055215.

Example A1

(S)-2-(1-(4-amino-3-(3-fluoro-4-isopropoxyphenyl)-1H-pyrazolo[3,4-d]pyrimidin-1-yl)ethyl)-3-(3-fluorophenyl)-4H-chromen-4-one To a solution of intermediate 13 (3.35 g, 11.60 mmol) in THF (2.0 ml), intermediate 7 (3.00 g, 10.55 mmol) and triphenylphosphine (5.57 g, 15.82 mmol) were added and stirred at RT for 5 min. Diisopropylazodicarboxylate (3.2 ml, 15.82 mmol) was added heated to 45° C. After 2 h, the reaction mixture was quenched with water and extracted with ethyl acetate. The organic layer was dried over sodium sulphate and concentrated under reduced pressure. The crude product was purified by column chromatography with ethyl acetate:petroleum ether to afford the title compound as off-white solid (2.79g, 48%). MP: 200-203° C. Mass: 554.3 (M$^+$+1). Enantiomeric excess: 94.0% as determined by HPLC on a chiralpak AD-H column, enriched in the fast eluting isomer (retention time=12.63 min).

Example A2

Method 1

(R)-2-(1-(4-amino-3-(3-fluoro-4-isopropoxyphenyl)-1H-pyrazolo[3,4-d]pyrimidin-1-yl)ethyl)-3-(3-fluorophenyl)-4H-chromen-4-one To intermediate 13 (0.039 g, 0.143 mmol), cesium hydroxide (0.013 g, 0.074 mmol) in ethanol was added and refluxed for 30 min. The solvent was concentrated and the residue was dissolved in DMF (0.5 ml). Intermediate 7a (0.050 g, 0.143 mmol) was added and stirred at room temperature for 4 h. The reaction mixture was diluted with water and extracted with ethyl acetate. The organic layer was dried over sodium sulphate and concentrated under reduced pressure. The crude product was purified by column chromatography with methanol: dichloromethane to afford the title compound as off-white solid (0.025 g, 231%). MP. 205-207° C. Mass: 554.3 ($M^+$+1). Enantiomeric excess: 74.0% as determined by HPLC on a chiralpak AD-H column, enriched in the late eluting isomer (retention time=14.77 min.).

Method 2

(R)-2-(1-(4-amino-3-(3-fluoro-4-isopropoxyphenyl)-1H-pyrazolo[3,4-d]pyrimidin-1-yl)ethyl)-3-(3-fluorophenyl)-4H-chromen-4-one To a solution of intermediate 13 (0.143 g, 0.527 mmol) in THF (7.5 ml), intermediate 10 (0.150 g, 0.527 mmol) and triphenylphosphine (0.200 g, 0.791 mmol) were added and stirred at RT for 5 min. Diisopropylazodicarboxylate (0.15 ml, 0.791 mmol) was added heated to 45° C. After 3 h, the reaction mixture was quenched with water and extracted with ethyl acetate. The organic layer was dried over sodium sulphate and concentrated under reduced pressure. The crude product was purified by column chromatography with ethyl acetate:petroleum ether to afford the title compound as off-white solid (0.035 g, 12%). MP: 204-206° C. Mass: 554.3 ($M^+$+1). Enantiomeric excess: 98.8% as determined by HPLC on a chiralpak AD-H column, enriched in the late eluting isomer (retention time=14.77 min.).

Example B 2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one To a solution of intermediate 13 (0.080 g, 0.293 mmol) in DMF (2 ml), potassium carbonate (0.081 g, 0.587 mmol) was added and stirred at RT for 10 min. To this mixture intermediate 2-(1-bromoethyl)-6-fluoro-3-(3-fluorophenyl)-4H-chromen-4-one (0.215 g, 0.587 mmol) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as a pale yellow solid (0.045 g, 270%). MP. 175-177° C. $^1$H-NMR (δ ppm, DMSO-$D_6$, 400 MHz): δ 8.20 (s, 1H), 7.85 (dd, J=8.1, 3.0 Hz, 1H), 7.48-7.33 (m, 5H), 7.14 (t, J=8.3 Hz, 1H), 7.02 (m, 2H), 6.90 (m, 1H), 6.10 (q, J=7.1 Hz, 1H), 5.42 (s, 2H), 4.64 (quintet, J=6.0 Hz, 1H), 1.99 (d, J=7.1 Hz, 3H), 1.42 (d, J=6.1 Hz, 6H).

Example B1

(S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one To a solution of intermediate 13 (0.134 g, 0.494 mmol) in THF (2.0 ml), intermediate 5 (0.150 g, 0.494 mmol) and triphenylphosphine (0.194 g, 0.741 mml) were added and stirred at RT for 5 min. Diisopropylazodicarboxylate (0.15 ml, 0.749 mmol) was added heated to 45° C. After 2 h, the reaction mixture was quenched with with water and extracted with ethyl acetate. The organic layer was dried over sodium sulphate and concentrated under reduced pressure. The crude product was purified by column chromatography with ethyl acetate:petroleum ether to afford the title compound as an off-white solid (0.049 g, 20%). MP: 139-142° C. Mass: 571.7 ($M^+$). $^1$H-NMR (δ ppm, $CDCl_3$, 400 MHz): 8.24 (s, 1H), 7.85 (dd, J=8.2, 3.1 Hz, 1H), 7.50-7.29 (m, 5H), 7.14 (t, J=8.4 Hz, 1H), 7.02 (m, 2H), 6.92 (d, J=8.4 Hz, 1H), 6.11 (q, J=7.1 Hz, 1H), 5.40 (s, 2H), 4.66 (quintet, J=6.1 Hz, 1H), 2.00 (d, J=7.1Hz, 3H), 1.42 (d, J=6.1 Hz, 6H). Enantiomeric excess: 89.8% as determined by HPLC on a chiralpak AD-H column, enriched in the fast eluting isomer (retention time=10.64 min.).

Example B2

(R)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one To a solution of intermediate 13 (0.284 g, 0.989 mmol) in THF (5.0 ml), intermediate 3 (0.250 g, 0.824 mmol) and tris(4-methoxy)phenylphosphine (0.435 g, 1.23 mml) were added and stirred at RT for 5 min. Diisopropylazodicarboxylate (0.25 ml, 1.23 mmol) was added stirred at room temperature. After 12 h, the reaction mixture was quenched with with water and extracted with ethyl acetate. The organic layer was dried over sodium sulphate and concentrated under reduced pressure. The crude product was purified by column chromatography with ethyl acetate:petroleum ether to afford the title compound as an off-white solid (0.105 g, 22%). MP: 145-148° C. Mass: 571.7 ($M^+$). $^1$H-NMR (δ ppm, $CDCl_3$, 400 MHz): 8.23 (s, 1H), 7.85 (dd, J=8.1, 3.0 Hz, 1H), 7.50-7.29 (m, 5H), 7.14 (t, J=8.4 Hz, 1H), 7.02 (m, 2H), 6.92 (d, J=8.4 Hz, 1H), 6.10 (q, J=7.1 Hz, 1H), 5.42 (s, 2H), 4.64 (quintet, J=6.1 Hz, 1H), 1.99 (d, J=7.2 Hz, 3H), 1.42 (d, J=6.0 Hz, 6H). Enantiomeric excess: 95.4% as determined by HPLC on a chiralpak AD-H column, enriched in the late eluting isomer (retention time=14.83 min.).

4-Methylbenzenesulfonate Salt of Compound B1

(S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one 4-methylbenzenesulfonate

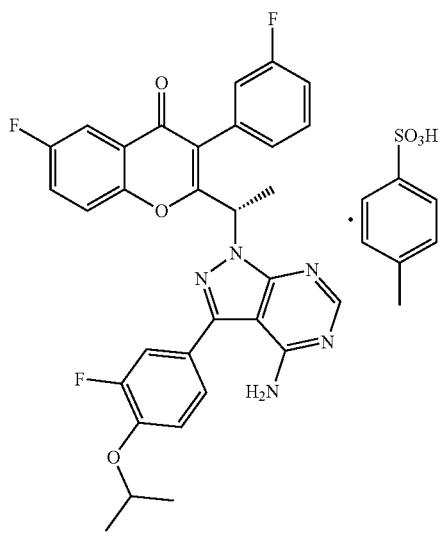

(S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one 4-methylbenzenesulfonate: To (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one (22.7 g, 39.69 mmol) in isopropanol (600 ml), p-toluenesulphonic acid (8.30 g, 43.66 mmol) was added and refluxed for 1 h. The reaction mixture was concentrated, co-distilled with petroleum ether and dried. To the residue water (300 ml) was added and stirred for 30 min. The solid was filtered, washed with petroleum ether and dried under vacuum to afford the title compound as off-white solid (28.2 g, 95%). MP: 138-141° C. $^1$H-NMR (δ ppm, CDCl$_3$, 400 MHz): 8.11 (s, 1H), 7.85 (dd, J=8.0, 3.0 Hz, 1H), 7.80 (d, J=8.2 Hz, 2H), 7.51 (dd, J=9.3,4.3 Hz, 1H), 7.45 (dd, J=7.5,3.1 Hz, 1H), 7.42-7.31 (m, 3H), 7.29 (m, 2H), 7.22 (d, J=8.0 Hz, 2H), 7.16 (t, J=8.3 Hz, 1H), 7.08 (dt, J=8.5, 2.5 Hz, 1H), 6.97 (br s, 1H), 6.88 (br s, 1H), 6.11 (q, J=7.2 Hz, 1H), 4.67 (quintet, J=6.0 Hz, 1H), 2.36 (s, 3H), 2.03 (d, J=7.1Hz, 3H), 1.43 (d, J=6.0 Hz, 6H). Mass: 572.4 (M$^+$+1-PTSA). Enantiomeric excess: 93.4% as determined by HPLC on a chiralpak AD-H column, enriched in the fast eluting isomer (retention time=12.35 min.)

Sulphate Salt of Compound B1

(S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one sulfate

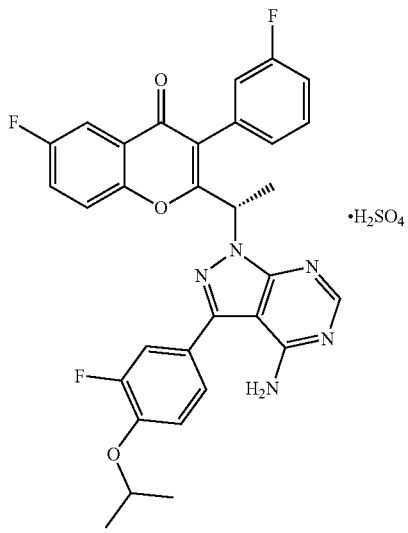

(S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one sulphate: To (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one (15.0 g, 26.24 mmol) in isopropanol (600 ml) was cooled to 0° C. To this Sulphuric acid (2.83 g, 28.86 mmol) was added and stirred at room temperature for 24 h. The reaction mass was filtered and washed with petroleum ether and dried under vacuum. To the solid, water (150 ml) was added and stirred for 30 min. The solid was filtered, washed with petroleum ether and dried under vacuum to afford the title compound as off-white solid (13.5 g, 76%). MP: 125-127° C. $^1$H-NMR (δ ppm, CDCl$_3$, 400 MHz): 8.11 (s, 1H), 7.85 (dd, J=8.0, 3.0 Hz, 1H), 7.51 (dd, J=9.2, 4.2 Hz, 1H), 7.45-7.31 (m, 3H), 7.29 (m, 1H), 7.15 (t, J=8.3 Hz, 1H), 7.08 (dt, J=8.5, 2.4 Hz, 1H), 6.96 (br s, 1H), 6.88 (br s, 1H), 6.09 (q, J=7.1 Hz, 1H), 4.676 (quintet, J=6.1 Hz, 1H), 2.01 (d, J=7.1 Hz, 3H), 1.42 (d, J=6.1 Hz, 6H). Mass: 572.2 (M$^+$+1-H$_2$SO$_4$). Enantiomeric excess: 89.6% as determined by HPLC on a chiralpak AD-H column, enriched in the fast eluting isomer (retention time=12.08 min.)

Various other acid addition salts of compound B1 were prepared as provided in Table 1.

TABLE 1

| Acid | Method of preparation | Melting Point (° C.) |
|---|---|---|
| Hydrochloric acid | Compound B1 (1 eq.) dissolved in THF, excess HCl/Et$_2$O was added, the clear solution obtained was evaporated completely. The residue obtained was washed with water. | 130-132 |

TABLE 1-continued

| Acid | Method of preparation | Melting Point (° C.) |
|---|---|---|
| p-Toluene-sulfonic acid | Compound B1 (1 eq.) dissolved in isopropyl alcohol (IPA), refluxed for 30 min., acid (1.1 eq.) in IPA was added, the clear solution obtained was evaporated completely. The residue obtained was washed with water. | 138-141° C. |
| Benzene-sulphonic acid | Compound B1 (1 eq.) dissolved in IPA, refluxed for 30 min., acid(1.1 eq.) in IPA was added, the clear solution not obtained, the residue was evaporated completely and was washed with water. | 170-172 |
| Maleic acid | Compound B1 (1 eq.) dissolved in IPA, refluxed for 30 min., acid (1.1 eq.) in IPA was added, the clear solution not obtained, the residue was evaporated completely and was washed with water. | 107-109 |
| Camphor sulfonic acid | Compound B1 (1 eq.) dissolved in IPA, refluxed for 30 min., acid (1.1 eq.) in IPA was added, the clear solution not obtained, the residue was evaporated completely and was washed with water. | 120-121 |
| Sulphuric acid | Compound B1 (1 eq.) dissolved in IPA, refluxed for 30 min., acid(1.1 eq.) in IPA was added, the clear solution obtained was evaporated completely. The residue obtained was washed with water. | 125-127 |

Metabolic Stability

Metabolic stability studies were conducted using mouse, rat, and human liver microsomes. The protocol for the studies with mouse, rat, and human liver microsomes (all from BD Gentest, USA) is provided below. In brief, 0.4 mg protein was preincubated with 2 mM NADPH (cofactor) in phosphate buffer (pH~7.4) for 15 min at 37° C. and then added with 1 μM test item and incubated further for 60 minutes in triplicate. The reaction mixture was terminated with methanol containing an internal standard and centrifuged further to analyze the test item remaining in the supernatant by LC-MS/MS. The percent parent compound remaining was calculated in comparison with similar samples terminated at 0 minutes. The results are provided in the tables below.

The data below surprisingly show that compound A1 of the present invention has significantly greater metabolic stability in human liver microsomes over its enantiomer A2 and racemic compound A. For instance, the compound of Example A1 has an almost 5 fold greater metabolic stability in human liver microsomes than that of Example A2. Due to their enhanced metabolic stability, the presently claimed compounds have a superior pharmacokinetic profile.

| Comparative data for Compound A and its individual isomers A1 & A2 | | | |
|---|---|---|---|
| | Metabolic stability in liver microsomes | | |
| Example | Mouse | Rat | Human |
| A | 32.6 | 43.1 | 38.4 |
| A1 | 46.1 | 35.8 | 54.5 |
| A2 | 34.7 | 44.2 | 11.4 |

Similarly, the data below surprisingly show that compound B1 of the present invention has significantly greater metabolic stability in human liver microsomes over its enantiomer B2 and racemic compound B. For instance, the compound of Example B1 has an almost 3 fold greater metabolic stability in human liver microsomes than that of Example B2. Due to their enhanced metabolic stability, the presently claimed compounds have a superior pharmacokinetic profile.

| Comparative data for Compound B and its individual isomers B1 & B2 | | | |
|---|---|---|---|
| | Metabolic stability in liver microsomes | | |
| Example | Mouse | Rat | Human |
| B | 54.9 | 51.4 | 46.9 |
| B1 | 36.6 | 23.1 | 74.9 |
| B2 | 54.1 | 48.6 | 27.5 |

Pharmacokinetics

The oral bioavailability of compound B1 (free base) and its PTSA salt were evaluated in rats. The protocol for the pharmacokinetics studies in rat is provided below.

All animals were fasted overnight (12 hours) before dosing and continued till 4.0 hours after administration of test item. Test item formulations were prepared in 1% Tween 80 and 99% media (0.5% Methyl cellulose, 4000 cPs, pH 2.2). The blood samples (150 μl from each animal) were collected from the orbital sinus, and placed into a micro centrifuge tube containing disodium EDTA as an anticoagulant. Blood samples were centrifuged immediately with a speed of 1000 g for 10 mM at 4° C. and separated plasma samples were frozen at below −80° C. and stored until analysis. The concentrations of test item in all formulation were analyzed by HPLC. The plasma concentrations of test item in all samples were analyzed by LC-MS/MS. Pharmacokinetic parameters viz. $C_{max}$, $AUC_{0-t}$, $T_{max}$, and $t_{1/2}$ were estimated by using WinNonlin software.

The PTSA salt of compound of Example B1 exhibited a $C_{max}$ about twice that, and an area under the curve (AUC) of nearly three times that, of the free base of compound B1.

Similarly the oral bioavailability of compound B1 (free base) and its PTSA salt were evaluated in Dogs. The PTSA salt of compound B1 exhibited a $C_{max}$ more than twice that, and an area under the curve (AUC) of about four times that, of the free base of compound B1.

Biological Assay

Assay 1: Fluorescent Determination of PI3K Enzyme Activity

The homogenous time resolved fluorescence (HTRF) assay allows detection of 3,4,5-triphosphate (PIP3) formed as a result of phosphorylation of phosphotidylinositol 4,5-biphosphate (PIP2) by PI3K isoforms such as α, β, γ or δ.

PI3K isoform activity for α, β, γ or δ was determined using a PI3K human HTRF™ Assay Kit (Millipore, Billerica, Mass.) with modifications. All incubations were carried out at room temperature. Briefly, 0.5 μl of 40× inhibitor (in 100% DMSO) or 100% DMSO were added to each well of a 384-well black plate (Greiner Bio-One, Monroe, N.C.) containing 14.5 μl 1× reaction buffer/PIP2 (10 mM $MgCl_2$, 5 mM DTT, 1.38 μM PIP2) mix with or without enzyme and incubated for 10 min. After the initial incubation, 5 μl/well of 400 μM ATP was added and incubated for an additional 30 minutes. Reaction was terminated by adding 5 μl/well stop solution (Millipore, Billerica, Mass.). Five microliters of detection mix (Millipore, Billerica, Mass.) were then added to each well and was incubated for 6-18 h in the dark. HRTF ratio was measured on a microplate reader (BMG Labtech., Germany) at an excitation wavelength of 337 nm and emission wavelengths of 665 and 620 nm with an integration time of 400 μsec.

The results are shown below.

Comparative data for Compound A and its individual isomers A1 & A2

|  |  | % Inhibition @ 1 μM | | |
|---|---|---|---|---|
| Example | Pi3K delta IC$_{50}$ (nM) | Pi3K α | Pi3K β | Pi3K γ |
| A | 37.32 | 2.63 | 9.95 | 55.85 |
| A1 | 13.83 | 8.91 | 47.87 | 80.60 |
| A2 | >10 μM | 0.95 | 38.74 | 66.3 |

| | Selectivity profile of Compound A1 | | | |
|---|---|---|---|---|
| | IC$_{50}$ (nM) | Fold-Selectivity | | |
| Assay | PI3Kδ | PI3Kα | PI3Kβ | PI3Kγ |
| Enzyme | 13.83 | >1000 | >54 | >9 |

Comparative Data for Compound B and its Individual Isomers B1 & B2

|  |  | % Inhibition @ 1 μM | | |
|---|---|---|---|---|
| Example | Pi3K δ IC$_{50}$ (nM) | Pi3K α | Pi3K β | Pi3K γ |
| B | 24.89 | 37.90 | 18 | 18.3 |
| B1 | 22.33 | 19.13 | 44.88 | 47.21 |
| B2 | 1447 | 25.29 | 52.01 | 68.10 |

| | Selectivity profile of Compound B1 | | | |
|---|---|---|---|---|
| | IC$_{50}$ (nM) | Fold-Selectivity | | |
| Assay | PI3Kδ | PI3Kα | PI3Kβ | PI3Kγ |
| Enzyme | 22.23 | >10000 | >50 | >48 |

Assay 2: In Vitro Cell Proliferation Assay in Leukemic Cell Lines

Growth inhibition assays were carried out using 10% FBS supplemented media. Cells were seeded at a concentration of 5000-20,000 cells/well in a 96-well plate. Test compound at a concentration range of from 0.01 to 10000 nM were added after 24 hours. Growth was assessed using the 3-[4,5-dimethylthiazol-2-yl]-2,5-diphenyltetrazolium bromide (MTT) dye reduction test at 0 h (prior to the addition of the test compound) and 48 h after the addition of test compound. Absorbance was read on a Fluostar Optima (BMG Labtech, Germany) at a wave length of 450 nm. Data were analysed using GraphPad Prism and percent inhibition due to the test compound compared to the control was calculated accordingly.

Results: While a slight dose-dependent reduction in cell viability was observed, the compounds did not display any apparent cytotoxicity over the 72 h incubation period.

Assay 3: Inhibition of AKT Phosphorylation in Leukemic Cell Lines:

Inhibition of AKT phosphorylation in leukemic cell lines: THP-1, HL-60, MOLT-4, RPMI-8226, or DLBCL cells were incubated with desired concentrations of compound for 48 hours. Cells were lysed and pAKT was determined by Western Blotting. Bands were quantified using ImageJ and normalized to actin.

Results: Compound A1 and Compound B1 when tested at 1 μM exhibited 50 to 90% inhibition.

Assay 4: Inhibition of PI3Kδ Signalling in Basophils from Human Whole Blood

PI3Kδ signalling in basophils manifested by an alteration of anti-FcεR1 induced CD63 expression is a useful pharmacodynamic marker determined using the Flow2CAST® kit (Buhlmann Laboratories, Switzerland). Briefly, it involves the following steps:

Mix the anti-coagulated blood sample by inverting the venipuncture tube several times Prepare fresh and pyrogen-free 3.5 ml polypropylene or polystyrene tubes suitable for Flow Cytometry measurements Add 49 μl of patient's whole blood to each tube.

Add 1 μl of 10% DMSO (background) or compound (10% DMSO) to the assigned tubes and mix gently. Incubate at room temperature for 15 min Pipette 50 μl of the Stimulation buffer (background) or anti-FcεRI Ab to each tube Add 100 μl of Stimulation Buffer to each tube Mix gently. Add 20 μl Staining Reagent (1:1 mix of FITC-CD63 and PE-CCR3) to each tube Mix gently, cover the tubes and incubate for 15 minutes at 37° C. in a water bath. (using an incubator will take about 10 minutes longer incubation time due to less efficient heat transfer)

Add 2 ml pre-warmed (18-28° C.) Lysing Reagent to each tube, mix gently

Incubate for 5-10 minutes at 18-28° C.

Centrifuge the tubes for 5 minutes at 500×g

Decant the supernatant by using blotting paper

Resuspend the cell pellet with 300-800 μl of Wash Buffer

Vortex gently and acquire the data on the flow cytometer within the same day.

Percent CD63 positive cells within the gated basophil population are to be determined in different treatment groups and normalized to vehicle control.

Results: Compound A1 and Compound B1 inhibited anti-FcεR1 mediated CD63 expression in human whole blood basophils with EC50s of ≤100 nM respectively.

Assay 4a: Cell Based Compound Specificity Towards Inhibition of PI3K δ, α, β or γ Isoforms Compound specificity towards PI3Kδ was determined in an IgM-induced B cell proliferation assay. B-cells isolated from blood of healthy subjects were seeded in a 96-well tissue culture plate and incubated with desired concentrations of compound for 30 min. Cells were stimulated with 5 μg/ml purified goat anti-human IgM. Growth was assessed using the 3-[4,5-dimethylthiazol-2-yl]-2,5-diphenyltetrazolium bromide (MTT) dye reduction test. For selectivity against PI3K α, β, or γ isoforms, NIH-3T3 or RAW macrophages were seeded in a 6-well tissue culture plate and incubated overnight. Complete medium was replaced with serum-free media the following day and compound at the desired concentrations were added. After 15 minutes, 20 ng/ml PDGF, 5 μM LPA, or 50 ng/ml c5a was added and incubated for an additional 10 minutes. Cells were lysed and AKT phosphorylation was determined by Western Blotting. Intensity of the bands was determined using ImageJ 1.42q (NIH, USA) and normalized to Actin (loading control).

|  | EC$_{50}$ (nM) | | Fold-Selectivity | |
| --- | --- | --- | --- | --- |
| Assay | PI3Kδ | PI3Kα | PI3Kβ | PI3Kγ |
| | Selectivity profile of Compound A1 | | | |
| Cell-based | <50 nM | >1000 | >30 | >8 |
| | Selectivity profile of Compound B1 | | | |
| Cell-based | <30 nM | >10000 | >34 | >17 |

Assay 5: Inhibition of Apoptosis in Leukemic Cell Lines

Apoptosis in leukemic cells was determined using an in situ Caspase 3 kit (Millipore, US) as outlined below:
  Seed leukemic cells at a density of 1×10$^6$ cells/well in a 6 well plate
  Add test compound/DMSO at desired concentrations
  Incubate the plate for 24 hrs at 37° C. in 5% CO$_2$ incubator
  Collect cells in a 2 ml centrifuge tube
  Add 1.6 μL of freshly prepared 5× FLICA reagent and mix cells by slightly flicking the tubes
  Incubate tubes for 1 hour at 37° C. under 5% CO$_2$
  Add 2 ml of 1× wash buffer to each tube and mix
  Centrifuge cells at <400×g for 5 minutes at room temperature.
  Carefully remove and discard supernatant, and gently vortex cell pellet to disrupt any cell-to-cell clumping.
  Resuspend cell pellet in 300 ul of 1× wash buffer
  Place 100 μL of each cell suspension into each of two wells of a black microtiter plate. Avoid creation of bubbles.
  Read absorbance of each microwell using an excitation wavelength of 490 nm and an emission wavelength of 520 nm
  Percent increase in caspase-3 activity manifested by an increase in fluorescence compared to the control blank is to be calculated.

Results: Compound A1 and Compound B1 dose-dependently induced Caspase-3 activity in the cell lines tested.

Assay 6: Screening for Anticancer Activity in Human Primary Leukemic Cells

6-I: Flow cytometry analysis of apoptotic induction in AML patient bone marrow leukemic cells upon compound treatment using Annexin V and 7-AAD staining: Mononuclear cells were extracted by the Ficoll method and seeded in plates. The cells were treated by different compounds for 48 hrs before they were analyzed by flow cytometry. After washing with PBS, 1×10$^5$ cells were stained by Annexin V-APC and 7-AAD. Annexin V positive staining measures total apoptotic cells, including early and late apoptotic cells. For Annexin V positive cells, 7-AAD negative signal reflects early apoptotic cells.

6-II: pAKT analysis of AML patient bone marrow sample using pAKT ELISA kit: Mononuclear cells were extracted by the Ficoll method and seeded in plates. The cells were treated by different compounds for 48 hrs before they were analyzed by pAKT ELISA kit following the product protocol. Briefly, 1×10$^6$ cells were transferred into an ELISA kit well and lyzed with 10 μL 5× Cell Lysis Mix (phospho-AKT 1/2/3 (Ser473) InstantOne™ ELISA Kit, eBioscience, 85-86042). The cells were then incubated with 50 μl antibody cocktail for 1 hr at room temp. on a microplate shaker (~300 rpm). After incubating with detection reagent, the result was measured using a SpectraMAX Plus microplate spectrophotometer set at 450 nm.

6-III: Cell proliferation analysis of AML patient bone marrow sample using MTS assay: Mononuclear cells were extracted by the Ficoll method and seeded in plates. The cells were treated by different compounds for 48 hrs and 72 hrs before they were analyzed by MTS assay following product instruction. Briefly, 20 μL of the MTS solution was added into each well containing the 100 μL cell suspension, followed by incubation for 4 hours at 37° C., in 95% humidity with presence of 5% CO$_2$. The absorbance of 490 nm (A490) was read using SpectraMAX Plus microplate spectrophotometer.

Results: Treatment with compound A1 and compound B1 caused a dose dependent reduction in proliferation and AKT phosphorylation with a concomitant increase in the number of apoptotic cells.

| Compound | Results |
| --- | --- |
| A1 | >50% inhibition of PAKT @ 0.3 μM; ~1.5 fold increase in appotosis @ 3 μM and Dose dependent reduction in cell viability. |
| B1 | >50% inhibition of PAKT @ 0.3 μM; ~1.5 fold increase in appotosis @ 3 μM and Dose dependent reduction in cell viability. |

Assay 6a: Screening for Anticancer Activity in Human Multiple Myeloma Cells

Samples were taken from two patients with newly diagnosed stage II IgG Kappa and stage III IgG Lambd restricted disease. This screening was performed by inducing apoptosis using doses and times determined from the MTT assay. 1-5×10$^5$ cells were collected by centrifugation. The cells were re-suspended in 500 μl of 1× Binding Buffer. 5 μl of Annexin V-FITC and 5 μl of propidium iodide were added. The cells were incubated at room temperature for 5 minutes in the dark.

Quantification by flow cytometry: Annexin V-FITC binding was analyzed by flow cytometry (Ex=488 nm; Em=530 nm) using FITC signal detector (usually FL1) and PI staining using a phycoerythrin emission signal detector (usually FL2). The results are shown below and in FIG. 1.

| B1 | >75% inhibition of PAKT @ 3.0 μM; ~1.5 fold increase in apoptosis @ 3 μM and Dose dependent reduction in cell viability. |
| --- | --- |

Assay 7: Screening for Anticancer Activity in Various Leukemic Cell Line

Proliferation of immortalized leukemic cells representative of various indications was determined by a MTT (3-(4,5-Dimethylthiazol-2-yl)-2,5-diphenyl tetrazolium bromide) assay. Cells were incubated with Compound B1 for different time-periods (72-96 h) based on their doubling time.

| Cell Line | Disease | Cell Type | Organ |
| --- | --- | --- | --- |
| TOLEDO | Diffuse large cell lymphoma/Non-Hodgkin's B-cell lymphoma | B lymphocyte | Peripheral Blood |
| U266B1 | Myeloma, Plasmacytoma (CD40-) | B lymphocyte | Peripheral Blood |
| MOLT-4 | ALL | T lymphoblast | Peripheral Blood |
| Jurkat | Acute T-cell leukemia | T lymphocyte | Peripheral Blood |

-continued

| Cell Line | Disease | Cell Type | Organ |
|---|---|---|---|
| THP-1 | Acute Monocytic Leukemia | Monocyte | Peripheral Blood |
| MM-1R | immunoglobulm A lambda myeloma | B lymphoblast | Peripheral Blood |
| DLBCL | Large Cell Lympoma | B lymphoblast | Ascites Fluid |
| MM-1S | immunoglobulm A lambda myeloma | B lymphoblast | Peripheral Blood |
| U937 | Histiocytic Lymphoma | Monocyte | Pleural Effusion |
| Raji | Burkitt's Lymphoma | B lymphoblast | Maxilla |
| CCRF-CEM | ALL | T lymphoblast | Peripheral Blood |
| HL-60 | AML | Promyeloblast | Peripheral Blood |

Results: Overall, a 50% growth inhibition for the majority of B, T, and monocytic cell lines was achieved at a concentration between 0.5-7.5 µM of Compound B1. The data demonstrated the ability of Compound B1 to inhibit leukemic cell proliferation albeit with different potencies based on the cell type.

Assay 8: Screening for Anticancer Activity in Human CLL Cells

Primary CLL cells were incubated with serial dilutions of test compound (Compound B1) for 48 hours and tested for apoptosis by activated caspase-3 and 7AAD staining measured by flow cytometry. After 72 hours of incubation, CLL cells were evaluated for cytotoxicity using the colorimetric MTS reagent. Phosphorylated Akt (S473) was measured by flow cytometry after one hour of incubation of test compound and ten minutes of incubation with anti-IgM or anti-IgD. Akt phosphorylation was quantified by median fluorescent intensity (MFI). Of the seven CLL patient samples used for experiments, five had mutated IGHV, five had 13q deletion or normal cytogenetics determined by fluorescent in situ hybridization, three were ZAP-70 negative, and seven were CD38 negative. IgM expression ranged between 13% and 90%, whereas IgD expression was uniformly elevated. The test compound significantly induced apoptosis (caspase-3+/7AAD+) and cytotoxicity in a dose-dependent manner in concentrations between 0.1 and 25.6 µM. Incubation with anti-surface immunoglobulin significantly induced Akt phosphorylation compared to media alone while the addition of test compound significantly abrogated this effect and returned Akt phosphorylation to baseline.

Figure 2A:
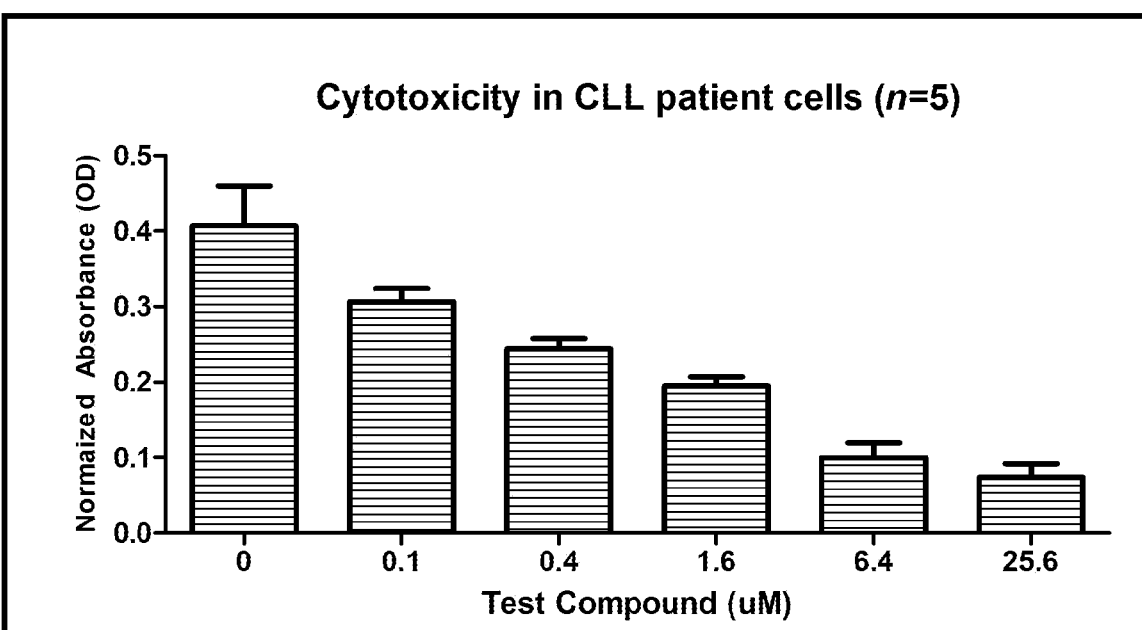
FIGS. 2A, 2B, and 2C are bar graphs showing the observed induction of cytotoxicity (FIG. 2A) and apopotosis (FIG. 2B) in CLL cells and the corresponding inhibition of PAkt (FIG. 2C), as measured by Assay 8.
Figure 2B:
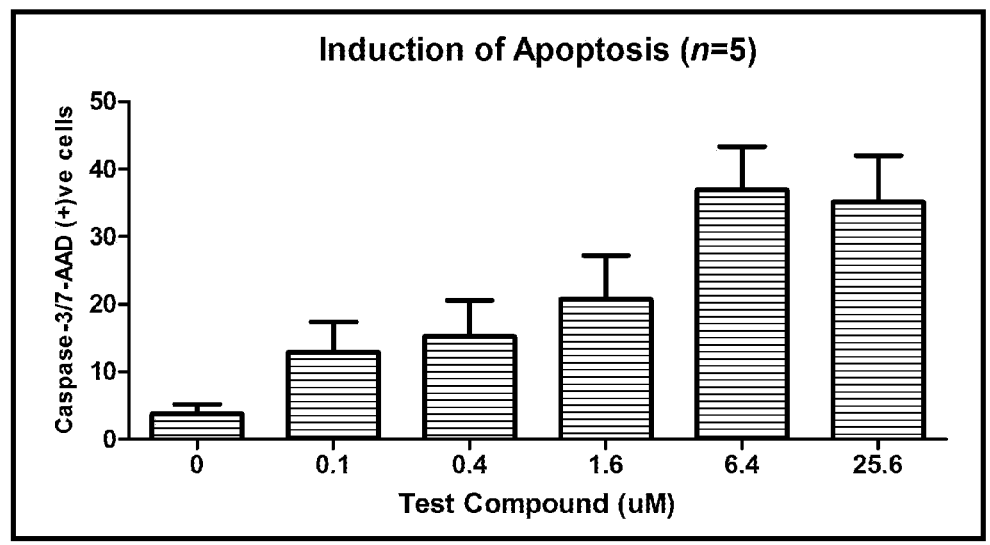
Figure 2C:
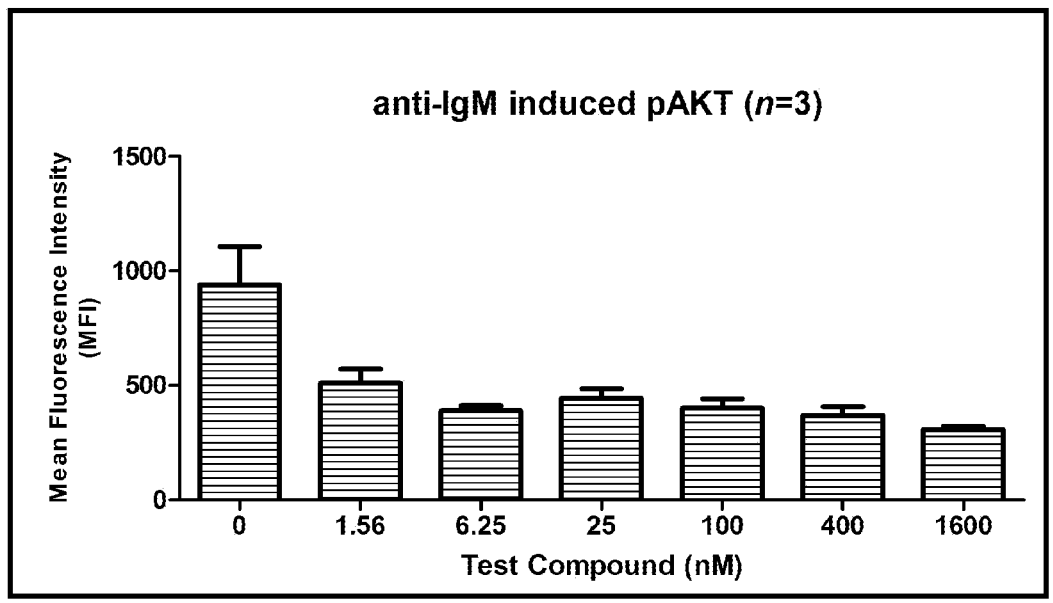

Results: The test compound induces cytotoxicity and apoptosis in CLL cells, via inhibition of pAKT. The results are also shown in FIGS. 2A, 2B, and 2C.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above. It is intended that the appended claims define the scope of the invention and that methods and structures within the scope of these claims and their equivalents be covered thereby.

All publications, patents and patent applications cited in this application are herein incorporated by reference to the same extent as if each individual publication, patent or patent application was specifically and individually indicated to be incorporated herein by reference.

The invention claimed is:

1. (S)-2-(1-(4-amino-3-(3-fluoro-4-isopropoxyphenyl)-1H-pyrazolo[3,4-d]-pyrimidin-1-yl)ethyl)-6-fluoro-3-(3-fluorophenyl)-4H-chromen-4-one.

2. A pharmaceutical composition comprising a compound of claim 1 and at least one pharmaceutically acceptable carrier.

3. The pharmaceutical composition of claim 2, wherein the compound has an enantiomeric excess of at least 98%.

4. A method treating indolent non-Hodgkin's lymphoma in a human subject in need thereof comprising administering to the human subject an effective amount of (S)-2-(1-(4-amino-3-(3-fluoro-4-isopropoxyphenyl)- 1H-pyrazolo [3,4-d]pyrimidin-1-yl)ethyl)-6-fluoro-3-(3-fluorophenyl)-4H-chromen-4-one or a pharmaceutically acceptable salt thereof.

5. The method of claim 4, wherein an effective amount of (S)-2-(1-(4-amino -3-(3-fluoro-4-isopropoxyphenyl)-1H-pyrazolo [3,4-d]pyrimidin-1-yl)ethyl)-6-fluoro-3-(3-fluorophenyl)-4H-chromen-4-one 4-methylbenzenesulfonate is administered.

6. The method of claim 5, wherein the (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one 4-methylbenzenesulfonate has an enantiomeric excess of at least 95%.

7. The method of claim 5, wherein the (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one 4-methylbenzenesulfonate has an enantiomeric excess of at least 98%.

8. The method of claim 4, further comprising the step of administering simultaneously or sequentially to the subject at least one other anti-cancer agent.

9. A method of treating follicular lymphoma in a human subject in need thereof comprising administering to the human subject an effective amount of (S)-2-(1-(4-amino-3-(3-fluoro -4-isopropoxyphenyl)-1H-pyrazolo [3,4-d]pyrimidin-1-yl)ethyl)-6-fluoro-3-(3-fluorophenyl)-4H -chromen-4-one or a pharmaceutically acceptable salt thereof.

10. The method of claim 9, wherein an effective amount of (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one 4-methylbenzenesulfonate is administered.

11. The method of claim 10, wherein the (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one 4-methylbenzenesulfonate has an enantiomeric excess of at least 95%.

12. The method of claim 10, wherein the (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H -chromen-4-one 4-methylbenzenesulfonate has an enantiomeric excess of at least 98%.

13. The method of claim 9, further comprising the step of administering simultaneously or sequentially to the subject at least one other anti-cancer agent.

* * * * *